US007112321B2

(12) United States Patent
Wang et al.

(10) Patent No.: US 7,112,321 B2
(45) Date of Patent: Sep. 26, 2006

(54) ADENO-ASSOCIATED VIRUS-MEDIATED DELIVERY OF GDNF TO SKELETAL MUSCLES

(75) Inventors: Lijun Wang, Chicago, IL (US); Shin-ichi Muramatsu, Minamikawachi-machi (JP); Imaharu Nakano, Saitama (JP); Hiroaki Mizukami, Minamikawachi-machi (JP); Keiya Ozawa, Minamikawachi-machi (JP)

(73) Assignee: Genzyme Corporation, Cambridge, MA (US)

( * ) Notice: Subject to any disclaimer, the term of this patent is extended or adjusted under 35 U.S.C. 154(b) by 161 days.

(21) Appl. No.: 10/327,620

(22) Filed: Dec. 19, 2002

(65) Prior Publication Data

US 2003/0161814 A1 Aug. 28, 2003

Related U.S. Application Data

(60) Provisional application No. 60/342,304, filed on Dec. 19, 2001.

(51) Int. Cl.
*A61K 48/00* (2006.01)
*C12N 15/864* (2006.01)

(52) U.S. Cl. .................... 424/93.2; 514/44; 435/320.1; 435/455; 435/456

(58) Field of Classification Search ............... 424/93.2; 514/44; 435/320.1
See application file for complete search history.

(56) References Cited

U.S. PATENT DOCUMENTS

| 5,858,351 | A * | 1/1999 | Podsakoff et al. .......... 424/93.2 |
| 5,858,775 | A | 1/1999 | Johnson |
| 6,180,613 | B1 | 1/2001 | Kaplitt et al. |
| 6,325,998 | B1 | 12/2001 | Podsakoff et al. |
| 6,552,003 | B1 * | 4/2003 | Finiels et al. ................ 514/44 |

OTHER PUBLICATIONS

Martinov et al., "Selective targeting of subpopulations of nerve and muscle cells in vivo by recombinant viral vectors," *Soc. Neurosci. Abstr.* 27(2): 2478, Nov. 2001.*
Acsadi et al., "GDNF gene therapy by adeno- and adeno-associated virus vectors improves the survival and motor functions of ALS (SOD1) mice," *J. Neurological Sciences* 1 (Suppl. 1):S34, 2002.
Alisky et al., "Gene therapy for amyotrophic lateral sclerosis and other motor neuron diseases," *Human Gene Therapy* 11:2315-2329, 2000.
Baumgartner et al., "Permanent rescue of lesioned neonatal motoneurons and enhanced axonal regeneration by adenovirus-mediated expression of glial cell-line-derived neurotrophic factor," *J. Neurosci. Res.* 54:766-777, 1998.

Blesch et al., "GDNF gene delivery to injured adults CNS motor neurons promotes axonal growth, expression of the trophic neuropeptide CGRP, and cellular protection," *J. Comp. Neurol.* 436:399-410, 2001.
Blits et al., "AAV-mediated overexpression of GDNF and BDNF rescues motorneurons following avulsion and reimplantation of rat lumbar ventral roots," abstract, *Society for Neuroscience* 27(2):2116, 2001.
Bohn, "A commentary on glial cell lin-derived neurotrophic factor (GDFN)," *Biochem. Pharmacol.* 57:135-142, 1999.
Büeler, "Adeno-associated viral vectors for gene transfer and gene therapy," *Biol. Chem.* 380:613-622, 1999.
Haase et al., "Gene therapy of murine motor neuron disease using adenoviral vectors for neurotrophic factors," *Nat. Med.* 3:429-436, 1997.
Henderson et al., "GDNF: a potent survival factor for motoneurons present in peripheral nerve and muscle," *Science* 266:1062-1064, 1994.
Kay et al., "Evidence for gene transfer and expression of factor IX in haemophilia B patients treated with an AAV vector," *Nat. Genet.* 24:257-261, 2000.
Keir et al., "Adeno-associated virus-mediated delivery of glial cell line-derived neuotrophic factor protects motor neuron-like cells from apoptosis," *J. NeuroVirology* 7:437-446, 2001.
Keller-Peck et al., "Glial cell line-derived neurotrophic factor administration in postnatal life results in motor unit enlargement and continuous synaptic remodeling at the neuromuscular junction," *J. Neurosci.* 21:6136-6146, 2001.
Lie et al., "GDNF expression is increased in denervated human skeletal muscle," *Neurosci. Lett.* 250:87-90, 1998.
Mandel et al., "Midbrain injection of recombinant adeno-associated virus encoding rat glial cell line-derived neurotrophic factor protects nigral neurons in a progressive 6-hydroxydopamine-induced degeneration model of Parkinson's disease in rats," *Proc. Natl. Acad. Sci. USA* 94:14083-14088, 1997.
Mohajeri et al., "Intramuscular grafts of myoblasts genetically modified to secrete glial cell line-derived neurotrophic factor prevent motoneuron loss and disease progression in a mouse model of familial amyotrophic lateral sclerosis," *Hum. Gene Ther.* 10:1853-1866, 1999.
Oppenheim et al., "Developing motor neurons rescued from programmed and axotomy-induced cell death by GDNF," *Nature* 373:344-346, 1995.
Sagot et al., "GDNF slows loss of motoneurons but not axonal degeneration or premature death of pmn/pmn mice," *J. Neurosci.* 16:2335-2341, 1996.

(Continued)

*Primary Examiner*—Scott D. Priebe
(74) *Attorney, Agent, or Firm*—Robins & Pasternak LLP

(57) ABSTRACT

Compositions and methods for delivering GDNF to skeletal muscles to result in a therapeutic effect are disclosed. The compositions and methods use adeno-associated virus (AAV)-based gene delivery systems. The methods are useful for treating motoneuron diseases, such as amyotrophic lateral sclerosis (ALS).

7 Claims, 7 Drawing Sheets

OTHER PUBLICATIONS

Sagot et al., "Differential effects of neurotrophic factors on motoneuron retrograde labeling in a murine model of motoneuron disease," *J. Neurosci.* 18:1132-1141, 1998.

Trupp et al., "Peripheral expression and biological activities of GDNF, a new neurotrophic factor for avian and mammalian peripheral neurons," *J. Cell Biol.* 130:137-148, 1995.

Wang et al., "Adeno-associated virus vector carrying human minidystrophin genes effectively ameliorates muscular dystrophy in mdx mouse model," *Proc. Natl. Acad. Sci. USA* 97:13714-13719, 2000.

Wang et l., "Neuroprotective effects of glial cell line-derived neurotrophic factor mediated by an adeno-associated virus vector in a transgenic animal model of amyotrophic laternal sclerosis," *J. Neuroscience* 22(16):6920-6928, 2002.

Xiao et al., "Efficient long-term gene transfer into muscle tissue of immunocompetent mice by adeno-associated virus vector," *J. Virol.* 70:8098-8108, 1996.

Yamamoto et al., "Expression of GDNF and GDNFR-$\alpha$ mRNAs in muscles of patients with motor neuron diseases," *Neurochem. Res.* 24:785-790, 1999.

Yan et al., "In vivo neutrophic effects of GDNF on neonatal and adult facial motor neurons," *Nature* 373:341-344, 1995.

Yuen, "The role of neurotrophic factors in disorders of peripheral nerves and motor neurons," *Phys. Med. Rehabil. Clin. N. Am.* 12:293-306, 2001.

\* cited by examiner

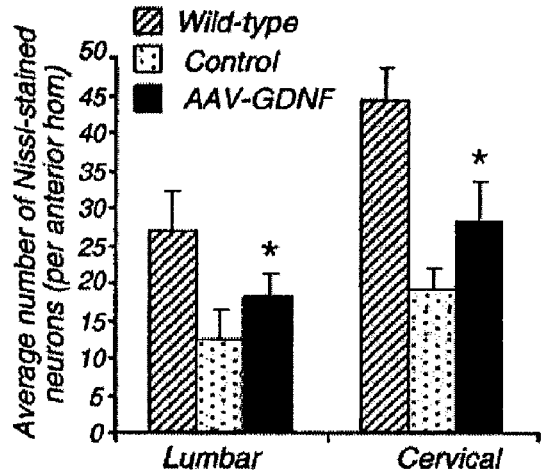
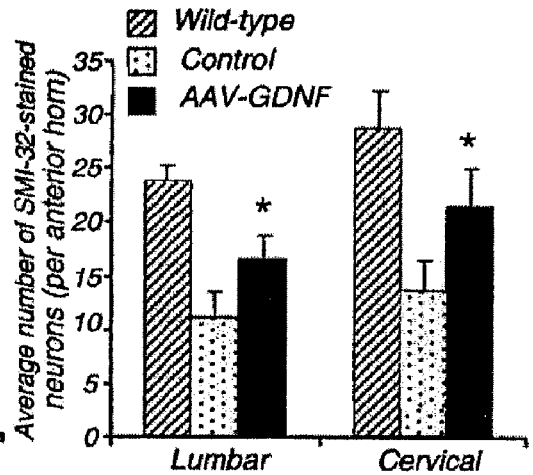
*FIG. 4A*
*FIG. 4B*
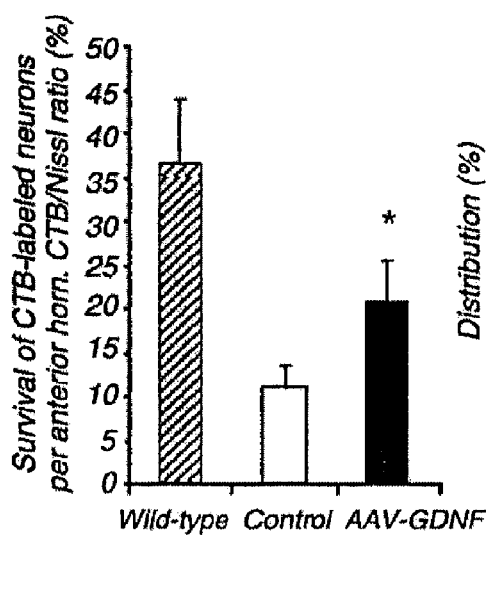
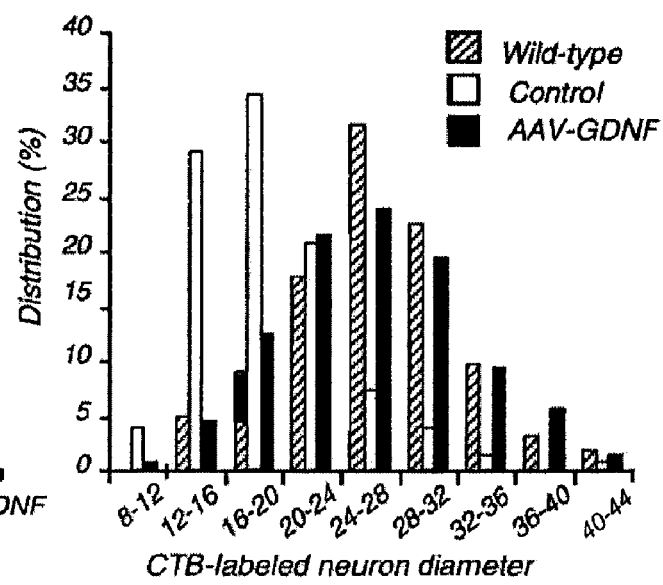
*FIG. 5A*
*FIG. 5B*

| | | | | | | | | | | | | | | | | |
|---|---|---|---|---|---|---|---|---|---|---|---|---|---|---|---|---|
| atg | aag | tta | tgg | gat | gtc | gtg | gct | gtc | tgc | ctg | gtg | ctg | ctc | cac | acc | 48 |
| Met | Lys | Leu | Trp | Asp | Val | Val | Ala | Val | Cys | Leu | Val | Leu | Leu | His | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcg | tcc | gcc | ttc | ccg | ctg | ccc | gcc | ggt | aag | agg | cct | ccc | gag | gcg | ccc | 96 |
| Ala | Ser | Ala | Phe | Pro | Leu | Pro | Ala | Gly | Lys | Arg | Pro | Pro | Glu | Ala | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| gcc | gaa | gac | cgc | tcc | ctc | ggc | cgc | cgc | gcg | ccc | ttc | gcg | ctg | agc | | 144 |
| Ala | Glu | Asp | Arg | Ser | Leu | Gly | Arg | Arg | Arg | Ala | Pro | Phe | Ala | Leu | Ser | |
| | | 35 | | | | 40 | | | | | 45 | | | | | |

| | | | | | | | | | | | | | | | | |
|---|---|---|---|---|---|---|---|---|---|---|---|---|---|---|---|---|
| agt | gac | tca | aat | atg | cca | gag | gat | tat | cct | gat | cag | ttc | gat | gat | gtc | 192 |
| Ser | Asp | Ser | Asn | Met | Pro | Glu | Asp | Tyr | Pro | Asp | Gln | Phe | Asp | Asp | Val | |
| | | 50 | | | | 55 | | | | | 60 | | | | | |

| | | | | | | | | | | | | | | | | |
|---|---|---|---|---|---|---|---|---|---|---|---|---|---|---|---|---|
| atg | gat | ttt | att | caa | gcc | acc | att | aaa | aga | ctg | aaa | agg | tca | cca | gat | 240 |
| Met | Asp | Phe | Ile | Gln | Ala | Thr | Ile | Lys | Arg | Leu | Lys | Arg | Ser | Pro | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aaa | caa | atg | gca | gtg | ctt | cct | aga | aga | gag | cgg | aat | cgg | cag | gct | gca | 288 |
| Lys | Gln | Met | Ala | Val | Leu | Pro | Arg | Arg | Glu | Arg | Asn | Arg | Gln | Ala | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| gct | gcc | aac | cca | gag | aat | tcc | aga | gga | aaa | ggt | cgg | aga | ggc | cag | agg | 336 |
| Ala | Ala | Asn | Pro | Glu | Asn | Ser | Arg | Gly | Lys | Gly | Arg | Arg | Gly | Gln | Arg | |
| | | | 100 | | | | | 105 | | | | | 110 | | | |

| | | | | | | | | | | | | | | | | |
|---|---|---|---|---|---|---|---|---|---|---|---|---|---|---|---|---|
| ggc | aaa | aac | cgg | ggt | tgt | gtc | tta | act | gca | ata | cat | tta | aat | gtc | act | 384 |
| Gly | Lys | Asn | Arg | Gly | Cys | Val | Leu | Thr | Ala | Ile | His | Leu | Asn | Val | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| gac | ttg | ggt | ctg | ggc | tat | gaa | acc | aag | gag | gaa | ctg | att | ttt | agg | tac | 432 |
| Asp | Leu | Gly | Leu | Gly | Tyr | Glu | Thr | Lys | Glu | Glu | Leu | Ile | Phe | Arg | Tyr | |
| | 130 | | | | | 135 | | | | | 140 | | | | | |

| | | | | | | | | | | | | | | | | |
|---|---|---|---|---|---|---|---|---|---|---|---|---|---|---|---|---|
| tgc | agc | ggc | tct | tgc | gat | gca | gct | gag | aca | acg | tac | gac | aaa | ata | ttg | 480 |
| Cys | Ser | Gly | Ser | Cys | Asp | Ala | Ala | Glu | Thr | Thr | Tyr | Asp | Lys | Ile | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aaa | aac | tta | tcc | aga | aat | aga | agg | ctg | gtg | agt | gac | aaa | gta | ggg | cag | 528 |
| Lys | Asn | Leu | Ser | Arg | Asn | Arg | Arg | Leu | Val | Ser | Asp | Lys | Val | Gly | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| gca | tgt | tgc | aga | ccc | atc | gcc | ttt | gat | gat | gac | ctg | tcg | ttt | tta | gat | 576 |
| Ala | Cys | Cys | Arg | Pro | Ile | Ala | Phe | Asp | Asp | Asp | Leu | Ser | Phe | Leu | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| gat | aac | ctg | gtt | tac | cat | att | cta | aga | aag | cat | tcc | gct | aaa | agg | tgt | 624 |
| Asp | Asn | Leu | Val | Tyr | His | Ile | Leu | Arg | Lys | His | Ser | Ala | Lys | Arg | Cys | |
| | | 195 | | | | | 200 | | | | | 205 | | | | |

| | | | | | |
|---|---|---|---|---|---|
| gga | tgt | atc | | | 633 |
| Gly | Cys | Ile | | | |
| 210 | | | | | |

FIG. 7

```
atg aag tta tgg gat gtc gtg gct gtc tgc ctg gtg ttg ctc cac acc      48
Met Lys Leu Trp Asp Val Val Ala Val Cys Leu Val Leu Leu His Thr
 1               5                  10                  15 gcg tct gcc ttc ccg ctg ccc gcc ggt aag agg ctt ctc gaa gcg ccc      96
Ala Ser Ala Phe Pro Leu Pro Ala Gly Lys Arg Leu Leu Glu Ala Pro
            20                  25                  30 gcc gaa gac cac tcc ctc ggc cac cgc cgc gtg ccc ttc gcg ctg acc     144
Ala Glu Asp His Ser Leu Gly His Arg Arg Val Pro Phe Ala Leu Thr
         35                  40                  45 agt gac tcc aat atg ccc gaa gat tat cct gac cag ttt gat gac gtc     192
Ser Asp Ser Asn Met Pro Glu Asp Tyr Pro Asp Gln Phe Asp Asp Val
     50                  55                  60 atg gat ttt att caa gcc acc atc aaa aga ctg aaa agg tca cca gat     240
Met Asp Phe Ile Gln Ala Thr Ile Lys Arg Leu Lys Arg Ser Pro Asp
 65                  70                  75                  80 aaa caa gcg gcg gca ctt cct cga aga gag agg aac cgg caa gct gca     288
Lys Gln Ala Ala Ala Leu Pro Arg Arg Glu Arg Asn Arg Gln Ala Ala
                 85                  90                  95 gct gcc agc cca gag aat tcc aga ggg aaa ggt cgc aga ggc cag agg     336
Ala Ala Ser Pro Glu Asn Ser Arg Gly Lys Gly Arg Arg Gly Gln Arg
            100                 105                 110 ggc aaa aat cgg ggg tgc gtc tta act gca ata cac tta aat gtc act     384
Gly Lys Asn Arg Gly Cys Val Leu Thr Ala Ile His Leu Asn Val Thr
        115                 120                 125 gac ttg ggt ttg ggc tac gaa acc aag gag gaa ctg atc ttt cga tat     432
Asp Leu Gly Leu Gly Tyr Glu Thr Lys Glu Glu Leu Ile Phe Arg Tyr
    130                 135                 140 tgt agc ggt tcc tgt gaa gcg gcc gag aca atg tac gac aaa ata cta     480
Cys Ser Gly Ser Cys Glu Ala Ala Glu Thr Met Tyr Asp Lys Ile Leu
145                 150                 155                 160 aaa aat ctg tct cga agt aga agg cta aca agt gac aag gta ggc cag     528
Lys Asn Leu Ser Arg Ser Arg Arg Leu Thr Ser Asp Lys Val Gly Gln
                165                 170                 175 gca tgt tgc agg ccg gtc gcc ttc gac gac gac ctg tcg ttt tta gac     576
Ala Cys Cys Arg Pro Val Ala Phe Asp Asp Asp Leu Ser Phe Leu Asp
            180                 185                 190 gac agc ctg gtt tac cat atc cta aga aag cat tcc gct aaa cgg tgt     624
Asp Ser Leu Val Tyr His Ile Leu Arg Lys His Ser Ala Lys Arg Cys
        195                 200                 205 gga tgt atc                                                          633
Gly Cys Ile
    210
```

FIG. 8

```
atg gga ttc ggg cca ctt gga gtt aat gtc caa ctg ggg gtc tac gga        48
Met Gly Phe Gly Pro Leu Gly Val Asn Val Gln Leu Gly Val Tyr Gly
 1               5                  10                  15 gac cgg atc cga ggt gcc gcc gcc gga cgg gac tct aag atg aag tta        96
Asp Arg Ile Arg Gly Ala Ala Ala Gly Arg Asp Ser Lys Met Lys Leu
                 20                  25                  30 tgg gat gtc gtg gct gtc tgc ctg gtg ttg ctc cac acc gcg tct gcc       144
Trp Asp Val Val Ala Val Cys Leu Val Leu Leu His Thr Ala Ser Ala
             35                  40                  45 ttc ccg ctg ccc gcc ggt aag agg ctt ctc gaa gcg ccc gct gaa gac       192
Phe Pro Leu Pro Ala Gly Lys Arg Leu Leu Glu Ala Pro Ala Glu Asp
         50                  55                  60 cac tcc ctc ggc cac cgc cgc gtg ccc ttc gcg ctg acc agt gac tcc       240
His Ser Leu Gly His Arg Arg Val Pro Phe Ala Leu Thr Ser Asp Ser
 65                  70                  75                  80 aat atg cct gaa gat tat cct gac cag ttt gat gac gtc atg gat ttt       288
Asn Met Pro Glu Asp Tyr Pro Asp Gln Phe Asp Asp Val Met Asp Phe
                 85                  90                  95 att caa gcc acc att aaa aga ctg aaa agg tca cca gat aaa caa gcg       336
Ile Gln Ala Thr Ile Lys Arg Leu Lys Arg Ser Pro Asp Lys Gln Ala
                100                 105                 110 gca gcg ctt cct cga aga gag agg aat cgg cag gct gca gct gcc agc       384
Ala Ala Leu Pro Arg Arg Glu Arg Asn Arg Gln Ala Ala Ala Ala Ser
             115                 120                 125 cca gag aat tcc aga ggg aaa ggt cgc aga ggc cag agg ggc aaa aat       432
Pro Glu Asn Ser Arg Gly Lys Gly Arg Arg Gly Gln Arg Gly Lys Asn
        130                 135                 140 cgg ggg tgc gtt tta act gcc ata cac tta aat gtc act gac ttg ggt       480
Arg Gly Cys Val Leu Thr Ala Ile His Leu Asn Val Thr Asp Leu Gly
145                 150                 155                 160 ttg ggc tat gaa acc aag gag gaa ctg atc ttt cga tat tgc agc ggt       528
Leu Gly Tyr Glu Thr Lys Glu Glu Leu Ile Phe Arg Tyr Cys Ser Gly
                165                 170                 175 tcc tgt gaa tcg gcc gag aca atg tat gac aaa ata cta aaa aac ctg       576
Ser Cys Glu Ser Ala Glu Thr Met Tyr Asp Lys Ile Leu Lys Asn Leu
                180                 185                 190 tct cgg agt aga agg cta aca agt gac aaa gta ggc cag gca tgt tgc       624
Ser Arg Ser Arg Arg Leu Thr Ser Asp Lys Val Gly Gln Ala Cys Cys
            195                 200                 205 agg ccg gtc gcc ttc gac gac gac ctg tcg ttt tta gat gac aac ctg       672
Arg Pro Val Ala Phe Asp Asp Asp Leu Ser Phe Leu Asp Asp Asn Leu
        210                 215                 220 gtt tac cat att cta aga aag cat tcc gct aaa cgg tgt gga tgt atc       720
Val Tyr His Ile Leu Arg Lys His Ser Ala Lys Arg Cys Gly Cys Ile
225                 230                 235                 240
```

FIG. 9

SEQUENCE LISTING

```
<160> NUMBER OF SEQ ID NOS: 7

<210> SEQ ID NO 1
<211> LENGTH: 633
<212> TYPE: DNA
<213> ORGANISM: Artificial Sequence
<220> FEATURE:
<221> NAME/KEY: CDS
<222> LOCATION: (1)..(633)
<220> FEATURE:
<223> OTHER INFORMATION: Description of Artificial Sequence: human GDNF

<400> SEQUENCE: 1 atg aag tta tgg gat gtc gtg gct gtc tgc ctg gtg ctg ctc cac acc      48
Met Lys Leu Trp Asp Val Val Ala Val Cys Leu Val Leu Leu His Thr
  1               5                  10                  15 gcg tcc gcc ttc ccg ctg ccc gcc ggt aag agg cct ccc gag gcg ccc      96
Ala Ser Ala Phe Pro Leu Pro Ala Gly Lys Arg Pro Pro Glu Ala Pro
             20                  25                  30 gcc gaa gac cgc tcc ctc ggc cgc cgc cgc gcg ccc ttc gcg ctg agc      144
Ala Glu Asp Arg Ser Leu Gly Arg Arg Arg Ala Pro Phe Ala Leu Ser
         35                  40                  45 agt gac tca aat atg cca gag gat tat cct gat cag ttc gat gat gtc      192
Ser Asp Ser Asn Met Pro Glu Asp Tyr Pro Asp Gln Phe Asp Asp Val
     50                  55                  60 atg gat ttt att caa gcc acc att aaa aga ctg aaa agg tca cca gat      240
Met Asp Phe Ile Gln Ala Thr Ile Lys Arg Leu Lys Arg Ser Pro Asp
 65                  70                  75                  80 aaa caa atg gca gtg ctt cct aga aga gag cgg aat cgg cag gct gca      288
Lys Gln Met Ala Val Leu Pro Arg Arg Glu Arg Asn Arg Gln Ala Ala
                 85                  90                  95 gct gcc aac cca gag aat tcc aga gga aaa ggt cgg aga ggc cag agg      336
Ala Ala Asn Pro Glu Asn Ser Arg Gly Lys Gly Arg Arg Gly Gln Arg
            100                 105                 110 ggc aaa aac cgg ggt tgt gtc tta act gca ata cat tta aat gtc act      384
Gly Lys Asn Arg Gly Cys Val Leu Thr Ala Ile His Leu Asn Val Thr
        115                 120                 125
```

-continued

```
gac ttg ggt ctg ggc tat gaa acc aag gag gaa ctg att ttt agg tac     432
Asp Leu Gly Leu Gly Tyr Glu Thr Lys Glu Glu Leu Ile Phe Arg Tyr
    130                 135                 140 tgc agc ggc tct tgc gat gca gct gag aca acg tac gac aaa ata ttg     480
Cys Ser Gly Ser Cys Asp Ala Ala Glu Thr Thr Tyr Asp Lys Ile Leu
145                 150                 155                 160 aaa aac tta tcc aga aat aga agg ctg gtg agt gac aaa gta ggg cag     528
Lys Asn Leu Ser Arg Asn Arg Arg Leu Val Ser Asp Lys Val Gly Gln
                165                 170                 175 gca tgt tgc aga ccc atc gcc ttt gat gat gac ctg tcg ttt tta gat     576
Ala Cys Cys Arg Pro Ile Ala Phe Asp Asp Asp Leu Ser Phe Leu Asp
            180                 185                 190 gat aac ctg gtt tac cat att cta aga aag cat tcc gct aaa agg tgt     624
Asp Asn Leu Val Tyr His Ile Leu Arg Lys His Ser Ala Lys Arg Cys
        195                 200                 205 gga tgt atc                                                         633
Gly Cys Ile
    210
```

<210> SEQ ID NO 2
<211> LENGTH: 211
<212> TYPE: PRT
<213> ORGANISM: Artificial Sequence
<220> FEATURE:
<223> OTHER INFORMATION: Description of Artificial Sequence: human GDNF

<400> SEQUENCE: 2

```
Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
    210
```

<210> SEQ ID NO 3

```
<211> LENGTH: 633
<212> TYPE: DNA
<213> ORGANISM: Artificial Sequence
<220> FEATURE:
<221> NAME/KEY: CDS
<222> LOCATION: (1)..(633)
<220> FEATURE:
<223> OTHER INFORMATION: Description of Artificial Sequence: rat GDNF

<400> SEQUENCE: 3 atg aag tta tgg gat gtc gtg gct gtc tgc ctg gtg ttg ctc cac acc     48
Met Lys Leu Trp Asp Val Val Ala Val Cys Leu Val Leu Leu His Thr
 1               5                  10                  15 gcg tct gcc ttc ccg ctg ccc gcc ggt aag agg ctt ctc gaa gcg ccc     96
Ala Ser Ala Phe Pro Leu Pro Ala Gly Lys Arg Leu Leu Glu Ala Pro
            20                  25                  30 gcc gaa gac cac tcc ctc ggc cac cgc cgc gtg ccc ttc gcg ctg acc    144
Ala Glu Asp His Ser Leu Gly His Arg Arg Val Pro Phe Ala Leu Thr
        35                  40                  45 agt gac tcc aat atg ccc gaa gat tat cct gac cag ttt gat gac gtc    192
Ser Asp Ser Asn Met Pro Glu Asp Tyr Pro Asp Gln Phe Asp Asp Val
    50                  55                  60 atg gat ttt att caa gcc acc atc aaa aga ctg aaa agg tca cca gat    240
Met Asp Phe Ile Gln Ala Thr Ile Lys Arg Leu Lys Arg Ser Pro Asp
65                  70                  75                  80 aaa caa gcg gcg gca ctt cct cga aga gag agg aac cgg caa gct gca    288
Lys Gln Ala Ala Ala Leu Pro Arg Arg Glu Arg Asn Arg Gln Ala Ala
                85                  90                  95 gct gcc agc cca gag aat tcc aga ggg aaa ggt cgc aga ggc cag agg    336
Ala Ala Ser Pro Glu Asn Ser Arg Gly Lys Gly Arg Arg Gly Gln Arg
            100                 105                 110 ggc aaa aat cgg ggg tgc gtc tta act gca ata cac tta aat gtc act    384
Gly Lys Asn Arg Gly Cys Val Leu Thr Ala Ile His Leu Asn Val Thr
        115                 120                 125 gac ttg ggt ttg ggc tac gaa acc aag gag gaa ctg atc ttt cga tat    432
Asp Leu Gly Leu Gly Tyr Glu Thr Lys Glu Glu Leu Ile Phe Arg Tyr
    130                 135                 140 tgt agc ggt tcc tgt gaa gcg gcc gag aca atg tac gac aaa ata cta    480
Cys Ser Gly Ser Cys Glu Ala Ala Glu Thr Met Tyr Asp Lys Ile Leu
145                 150                 155                 160 aaa aat ctg tct cga agt aga agg cta aca agt gac aag gta ggc cag    528
Lys Asn Leu Ser Arg Ser Arg Arg Leu Thr Ser Asp Lys Val Gly Gln
                165                 170                 175 gca tgt tgc agg ccg gtc gcc ttc gac gac gac ctg tcg ttt tta gac    576
Ala Cys Cys Arg Pro Val Ala Phe Asp Asp Asp Leu Ser Phe Leu Asp
            180                 185                 190 gac agc ctg gtt tac cat atc cta aga aag cat tcc gct aaa cgg tgt    624
Asp Ser Leu Val Tyr His Ile Leu Arg Lys His Ser Ala Lys Arg Cys
        195                 200                 205 gga tgt atc                                                         633
Gly Cys Ile
    210

<210> SEQ ID NO 4
<211> LENGTH: 211
<212> TYPE: PRT
<213> ORGANISM: Artificial Sequence
<220> FEATURE:
<223> OTHER INFORMATION: Description of Artificial Sequence: rat GDNF

<400> SEQUENCE: 4

Met Lys Leu Trp Asp Val Val Ala Val Cys Leu Val Leu Leu His Thr
 1               5                  10                  15
```

-continued

Ala Ser Ala Phe Pro Leu Pro Ala Gly Lys Arg Leu Leu Glu Ala Pro
            20                  25                  30

Ala Glu Asp His Ser Leu Gly His Arg Arg Val Pro Phe Ala Leu Thr
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Ala Ala Ala Leu Pro Arg Arg Glu Arg Asn Arg Gln Ala Ala
                85                  90                  95

Ala Ala Ser Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Glu Ala Ala Glu Thr Met Tyr Asp Lys Ile Leu
145                 150                 155                 160

Lys Asn Leu Ser Arg Ser Arg Arg Leu Thr Ser Asp Lys Val Gly Gln
                165                 170                 175

Ala Cys Cys Arg Pro Val Ala Phe Asp Asp Leu Ser Phe Leu Asp
            180                 185                 190

Asp Ser Leu Val Tyr His Ile Leu Arg Lys His Ser Ala Lys Arg Cys
    195                 200                 205

Gly Cys Ile
    210

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: flag

<400> SEQUENCE: 5

Asp Tyr Lys Asp Asp Asp Asp Lys
1               5

<210> SEQ ID NO 6
<211> LENGTH: 720
<212> TYPE: DNA
<213> ORGANISM: Artificial Sequence
<220> FEATURE:
<221> NAME/KEY: CDS
<222> LOCATION: (1)..(720)
<220> FEATURE:
<223> OTHER INFORMATION: Description of Artificial Sequence: mouse GDNF

<400> SEQUENCE: 6 atg gga ttc ggg cca ctt gga gtt aat gtc caa ctg ggg gtc tac gga      48
Met Gly Phe Gly Pro Leu Gly Val Asn Val Gln Leu Gly Val Tyr Gly
1               5                   10                  15 gac cgg atc cga ggt gcc gcc gcc gga cgg gac tct aag atg aag tta      96
Asp Arg Ile Arg Gly Ala Ala Ala Gly Arg Asp Ser Lys Met Lys Leu
            20                  25                  30 tgg gat gtc gtg gct gtc tgc ctg gtg ttg ctc cac acc gcg tct gcc     144
Trp Asp Val Val Ala Val Cys Leu Val Leu Leu His Thr Ala Ser Ala
        35                  40                  45 ttc ccg ctg ccc gcc ggt aag agg ctt ctc gaa gcg ccc gct gaa gac     192

```
                                                              -continued

Phe Pro Leu Pro Ala Gly Lys Arg Leu Leu Glu Ala Pro Ala Glu Asp
         50                  55                  60 cac tcc ctc ggc cac cgc cgc gtg ccc ttc gcg ctg acc agt gac tcc          240
His Ser Leu Gly His Arg Arg Val Pro Phe Ala Leu Thr Ser Asp Ser
 65              70                  75                  80 aat atg cct gaa gat tat cct gac cag ttt gat gac gtc atg gat ttt          288
Asn Met Pro Glu Asp Tyr Pro Asp Gln Phe Asp Asp Val Met Asp Phe
                 85                  90                  95 att caa gcc acc att aaa aga ctg aaa agg tca cca gat aaa caa gcg          336
Ile Gln Ala Thr Ile Lys Arg Leu Lys Arg Ser Pro Asp Lys Gln Ala
                100                 105                 110 gca gcg ctt cct cga aga gag agg aat cgg cag gct gca gct gcc agc          384
Ala Ala Leu Pro Arg Arg Glu Arg Asn Arg Gln Ala Ala Ala Ala Ser
            115                 120                 125 cca gag aat tcc aga ggg aaa ggt cgc aga ggc cag agg ggc aaa aat          432
Pro Glu Asn Ser Arg Gly Lys Gly Arg Arg Gly Gln Arg Gly Lys Asn
        130                 135                 140 cgg ggg tgc gtt tta act gcc ata cac tta aat gtc act gac ttg ggt          480
Arg Gly Cys Val Leu Thr Ala Ile His Leu Asn Val Thr Asp Leu Gly
145                 150                 155                 160 ttg ggc tat gaa acc aag gag gaa ctg atc ttt cga tat tgc agc ggt          528
Leu Gly Tyr Glu Thr Lys Glu Glu Leu Ile Phe Arg Tyr Cys Ser Gly
                165                 170                 175 tcc tgt gaa tcg gcc gag aca atg tat gac aaa ata cta aaa aac ctg          576
Ser Cys Glu Ser Ala Glu Thr Met Tyr Asp Lys Ile Leu Lys Asn Leu
            180                 185                 190 tct cgg agt aga agg cta aca agt gac aaa gta ggc cag gca tgt tgc          624
Ser Arg Ser Arg Arg Leu Thr Ser Asp Lys Val Gly Gln Ala Cys Cys
        195                 200                 205 agg ccg gtc gcc ttc gac gac gac ctg tcg ttt tta gat gac aac ctg          672
Arg Pro Val Ala Phe Asp Asp Asp Leu Ser Phe Leu Asp Asp Asn Leu
210                 215                 220 gtt tac cat att cta aga aag cat tcc gct aaa cgg tgt gga tgt atc          720
Val Tyr His Ile Leu Arg Lys His Ser Ala Lys Arg Cys Gly Cys Ile
225                 230                 235                 240

<210> SEQ ID NO 7
<211> LENGTH: 240
<212> TYPE: PRT
<213> ORGANISM: Artificial Sequence
<220> FEATURE:
<223> OTHER INFORMATION: Description of Artificial Sequence: mouse GDNF

<400> SEQUENCE: 7

Met Gly Phe Gly Pro Leu Gly Val Asn Val Gln Leu Gly Val Tyr Gly
 1               5                  10                  15

Asp Arg Ile Arg Gly Ala Ala Gly Arg Asp Ser Lys Met Lys Leu
                20                  25                  30

Trp Asp Val Val Ala Val Cys Leu Val Leu Leu His Thr Ala Ser Ala
             35                  40                  45

Phe Pro Leu Pro Ala Gly Lys Arg Leu Leu Glu Ala Pro Ala Glu Asp
         50                  55                  60

His Ser Leu Gly His Arg Arg Val Pro Phe Ala Leu Thr Ser Asp Ser
 65              70                  75                  80

Asn Met Pro Glu Asp Tyr Pro Asp Gln Phe Asp Asp Val Met Asp Phe
                 85                  90                  95

Ile Gln Ala Thr Ile Lys Arg Leu Lys Arg Ser Pro Asp Lys Gln Ala
                100                 105                 110

Ala Ala Leu Pro Arg Arg Glu Arg Asn Arg Gln Ala Ala Ala Ala Ser
```

-continued

```
                    115                 120                 125
Pro Glu Asn Ser Arg Gly Lys Gly Arg Arg Gly Gln Arg Gly Lys Asn
        130                 135                 140

Arg Gly Cys Val Leu Thr Ala Ile His Leu Asn Val Thr Asp Leu Gly
145                 150                 155                 160

Leu Gly Tyr Glu Thr Lys Glu Glu Leu Ile Phe Arg Tyr Cys Ser Gly
                165                 170                 175

Ser Cys Glu Ser Ala Glu Thr Met Tyr Asp Lys Ile Leu Lys Asn Leu
            180                 185                 190

Ser Arg Ser Arg Arg Leu Thr Ser Asp Lys Val Gly Gln Ala Cys Cys
        195                 200                 205

Arg Pro Val Ala Phe Asp Asp Asp Leu Ser Phe Leu Asp Asp Asn Leu
        210                 215                 220

Val Tyr His Ile Leu Arg Lys His Ser Ala Lys Arg Cys Gly Cys Ile
225                 230                 235                 240
```

ADENO-ASSOCIATED VIRUS-MEDIATED DELIVERY OF GDNF TO SKELETAL MUSCLES

CROSS-REFERENCE TO RELATED APPLICATION

This application is related to provisional patent application Ser. No. 60/342,304, filed Dec. 19, 2001, from which application priority is claimed under 35 USC §119(e)(1) and which application is incorporated herein by reference in its entirety.

TECHNICAL FIELD

The present invention relates generally to compositions and methods for gene delivery. In particular, the present invention pertains to adeno-associated virus (AAV)-based gene delivery systems for delivering glial cell line-derived neurotrophic factor (GDNF) to skeletal muscle to treat motoneuron diseases such as amyotrophic lateral sclerosis (ALS).

BACKGROUND OF THE INVENTION

Motoneuron neurodegenerative diseases present major public health issues. For example, amyotrophic lateral sclerosis (ALS) is a relentlessly progressive lethal disease that involves selective annihilation of motoneurons. Approximately 20% of familial ALS is linked to mutations in the Cu/Zn superoxide dismutase (SOD1) gene (Julien, J. P., *Cell* (2001) 104:581–591). Transgenic mice overexpressing this mutant gene (mSOD1G93A) develop a dominantly inherited adult-onset paralytic disorder that has many of the clinical and pathological features of familial ALS (Gurney et al., *Science* (1994) 264:1772–1775). However, to date, the molecular mechanisms leading to motoneuron degeneration in ALS and most motor neuron diseases remain poorly understood. Because the mechanism leading to motoneuron degeneration in ALS is not known, there is currently no therapy available to prevent or cure ALS.

Glial cell line-derived neurotrophic factor (GDNF) has been shown to be the most potent neurotrophic factor for the proliferation, differentiation, and survival of spinal motoneurons. GDNF and GDNF mRNA levels have been reported to be up-regulated in denervated muscles as found in ALS, polymyostits (PM) and muscular dystrophy (MD), or after peripheral nerve lesion and the like (Trupp et al., *J. Cell Biol.* (1995) 130:137–148; Lie and Weis, *Neurosci. Lett.* (1998) 250: 87–90; Yamamoto et al., *Neurochem. Res.* (1999) 24:785–790). GDNF has been proposed as a therapeutic agent to treat motor neuron disease (Henderson et al., *Science* (1994) 266:1062–1064; Oppenheim et al., *Nature* (1995) 373:344–346; Yan et al., *Nature* (1995) 373:341–344; Sagot et al., *J. Neurosci.* (1996) 16: 2335–2341; Bohn, M. C., *Biochem. Pharmacol.* (1999) 57:135–142; Mohajeri et al., *Hum. Gene Ther.* (1999) 10:1853–1866). Neurotrophic factors such as GDNF have been shown to slow motoneuron degeneration and to restore the function of non-functional motoneurons that are still alive (Trupp et al., *J. Cell Biol.* (1995) 130:137–148; Sagot et al., *J. Neurosci.* (1998) 18: 1132–1141; Lie and Weis, *Neurosci. Lett.* (1998) 250: 87–90; Baumgartner and Shine, *J. Neurosci. Res.* (1998) 54: 766–777; Yamamoto et al., *Neurochem. Res.* (1999) 24:785–790; Biesch and Tuszynski, *J. Comp. Neurol.* (2001) 436:399–410; Keller-Peck et al., *J. Neurosci.* (2001) 21:6136–6146.

To date, however, clinical trials using repeated administration of recombinant GDNF, as well as other neurotrophic factors such as ciliary neurotrophic factor (CNTF), brain-derived neurotrophic factor (BDNF) and insulin-like growth factor-I (IGF-I), have shown limited or no promise and/or have resulted in severe side-effects (Yuen, E. C., *Phys. Med. Rehabil. Clin. N. Am.* (2001) 12:293–306). In particular, these proteins have a short in vivo plasma half-life, have poor access to spinal cord motoneurons, and cause inflammatory reactions that prevent administration at an adequate dose (Haase et al., *Nat. Med.* (1997) 3:429–436; Alisky and Davidson, *Hum. Gene Ther.* (2000) 11:2315–2329). These limitations, together with the chronicity and progressive nature of most motoneuron degenerative diseases, underscore the necessity to develop innovative strategies that offer more effective and long-term delivery of neurotrophic factors to motoneurons. In an attempt to overcome the above-described problems, experimenters have studied gene-therapy approaches for treating ALS (Alisky and Davidson, *Hum. Gene Ther.* (2000) 11:2315–2329). Genetically modified myoblast-based GDNF gene delivery in muscles prevented loss of spinal motoneurons and delayed the onset of the disease in a transgenic mouse familial ALS model (Mohajeri et al., *Hum. Gene Ther.* (1999) 10:1853–1866). However, the level of GDNF protein in treated muscle was undetectable.

Adeno-associated virus (AAV) has shown promise for delivering genes for gene therapy in clinical trials in humans (see, e.g., Kay et al., *Nat. Genet.* (2000) 24:257–261). As the only viral vector system based on a nonpathogenic and replication-defective virus, recombinant AAV virions have been successfully used to establish efficient and sustained gene transfer of both proliferating and terminally differentiated cells in a variety of tissues (Bueler, H., *Biol. Chem.* (1999) 380:613–622). Notwithstanding these successes, AAV-mediated GDNF gene therapy for treating motor neuron disease, such as ALS, has not been demonstrated.

The AAV genome is a linear, single-stranded DNA molecule containing about 4681 nucleotides. The AAV genome generally comprises an internal nonrepeating genome flanked on each end by inverted terminal repeats (ITRs). The ITRs are approximately 145 base pairs (bp) in length. The ITRs have multiple functions, including as origins of DNA replication, and as packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV has been engineered to deliver genes of interest by deleting the internal nonrepeating portion of the AAV genome (i.e., the rep and cap genes) and inserting a heterologous gene between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

AAV is a helper-dependent virus; that is, it requires coinfection with a helper virus (e.g., adenovirus, herpesvirus or vaccinia), in order to form AAV virions. In the absence of coinfection with a helper virus, AAV establishes a latent state in which the viral genome inserts into a host cell chromosome, but infectious virions are not produced. Subsequent infection by a helper virus "rescues" the integrated genome, allowing it to replicate and package its genome into an infectious AAV virion. While AAV can infect cells from different species, the helper virus must be of the same species as the host cell. Thus, for example, human AAV will replicate in canine cells coinfected with a canine adenovirus.

However, prior to the present invention, AAV-mediated delivery of GDNF for the treatment of motoneuron diseases, such as ALS, has not been successfully achieved.

SUMMARY OF THE INVENTION

Accordingly, the present invention provides a potent and effective method for treating neurodegenerative diseases that affect motoneurons. As shown herein, skeletal muscle is particularly useful for AAV-mediated GDNF delivery. Skeletal muscle is highly transducible, easily accessible and displays a low cell turnover (Wang et al., *Proc. Natl. Acad. Sci. USA* (2000) 97:13714–13719; Xiao et al., *J. Virol.* (1996) 70:8098–8108). Nerve terminals are only in contact with myofibers at the neuromuscular junctions (NMJs) at which barriers against various substances is absent, allowing them to reach the central nervous system. According to the neurotrophic theory, neurites connect with their targets to gain access to target-derived neurotrophic factors for neuron survival. As a target-derived neurotrophic factor, endogenous GDNF produced by skeletal muscle functions via retrograde axonal transport from the target muscle tissue to motoneuronal cell bodies in the spinal cord (Mitsumoto, H., *Muscle Nerve* (1999) 22:1000–1021). The inventors herein have discovered that AAV-mediated GDNF gene delivery via intramuscular administration drives substantial and persistent expression of GDNF in large numbers of myofibers. Moreover, expressed GDNF is retrogradely transported to spinal cord motoneurons from nerve terminals in the muscle. Significantly, the inventors herein demonstrate through studies in ALS animal models that AAV-mediated GDNF delivery via skeletal muscle significantly delays the onset of disease, lengthens the life-span, abates behavioral impairment, and promotes motoneuron survival.

Accordingly, in one embodiment, the invention is directed to a method of delivering a recombinant AAV virion to a muscle cell or muscle tissue of a mammalian subject with a motoneuron disorder. The method comprises:

(a) providing a recombinant AAV virion which comprises a polynucleotide encoding a GDNF operably linked to control elements capable of directing the in vivo transcription and translation of the GDNF; and (b) delivering the recombinant AAV virion directly into the muscle cell or muscle tissue of the subject, whereby the GDNF is expressed at a level which provides a therapeutic effect in the mammalian subject.

In certain embodiments, the muscle cell or tissue is derived from skeletal muscle. In yet additional embodiments, the recombinant AAV virion is introduced into the muscle cell in vivo, e.g., by intramuscular injection. In alternative embodiments, the recombinant AAV virion is introduced into the muscle cell in vitro. In yet further embodiments, the motoneuron disorder is amyotrophic lateral sclerosis (ALS).

In another embodiment, the invention is directed to a method of delivering a recombinant AAV virion to a skeletal muscle of a human subject with ALS. The method comprises:

(a) providing a recombinant AAV virion that comprises a polynucleotide encoding a human GDNF operably linked to control elements capable of directing the in vivo transcription and translation of said GDNF; and (b) delivering the recombinant AAV virion directly into skeletal muscle of the subject in vivo, whereby the GDNF is expressed at a level which provides a therapeutic effect in the human subject.

In yet another embodiment, the invention is directed to a method of treating a mammalian subject with a motoneuron disorder comprising administering intramuscularly to the subject recombinant adeno-associated virus (AAV) virions comprising a polynucleotide encoding a GDNF polypeptide operably linked to expression control elements capable of directing the in vivo transcription and translation of the GDNF to provide a therapeutic effect.

In certain embodiments, the motoneuron disorder is ALS. In additional embodiments, the subject is human and the polynucleotide encodes a human GDNF, such as human pre-pro-GDNF. Additionally, the control elements can comprise a viral promoter, such as an MLP, CMV, or RSV LTR promoter. In yet additional embodiments, muscle cells are transduced in vivo, e.g., by administration into skeletal muscle.

In another embodiment, the invention is directed to a method of treating a mammalian subject with ALS. The method comprises administering into skeletal muscle of the subject a composition comprising recombinant adeno-associated virus (AAV) virions that comprise a polynucleotide encoding a GDNF polypeptide operably linked to expression control elements capable of directing the in vivo transcription and translation of the GDNF, to provide a therapeutic effect.

In certain embodiments, the subject is a human and the polynucleotide encodes a human GDNF, such as human pre-pro-GDNF. Additionally, the control elements can comprise a viral promoter, such as an MLP, CMV, or RSV LTR promoter.

These and other embodiments of the subject invention will readily occur to those of skill in the art in view of the disclosure herein.

BRIEF DESCRIPTION OF THE FIGURES

FIGS. 4A–4B show the numbers of spinal motoneurons in wild-type, control ALS and AAV-GDNF-treated ALS mice. FIG. 4A shows the average number of Nissl-stained neurons per anterior horn. FIG. 4B shows the average number of SMI-32-stained neurons per anterior horn.

FIGS. 5A and 5B display the effect of GDNF on motoneurons that retained axonal projections in wild-type, control ALS and AAV-GDNF-treated ALS mice. FIG. 5A shows the survival of CTB-labeled motoneurons per anterior horn. The value represents the CTB/Nissl ratio (average number of neurons per anterior horn). FIG. 5B shows the percent distribution of muscle fibers of various diameters in wild-type, control ALS and AAV-GDNF-treated ALS mice.

FIG. 6A displays the cumulative probability of onset of rotarod deficits in ALS mice. FIG. 6B shows performance of ALS mice in the rotarod test at 5 rpm. FIG. 6C shows performance of ALS mice in the rotarod test at 10 rpm. FIG. 6D shows performance of ALS mice in the rotarod test at 20 rpm. FIG. 6E shows the cumulative probability of survival.

FIG. 7 (SEQ ID NOS:1 and 2) shows the nucleotide sequence and amino acid sequence for a human pre-pro-GDNF. The mature GDNF molecule spans amino acid positions 78–211.

FIG. 8 (SEQ ID NOS:3 and 4) shows the nucleotide sequence and amino acid sequence for a rat pre-pro-GDNF. The mature GDNF molecule spans amino acid positions 78–211.

FIG. 9 (SEQ ID NOS:6 and 7) shows the nucleotide sequence and amino acid sequence for a mouse pre-pro-GDNF. The mature GDNF molecule spans amino acid positions 107–240.

DETAILED DESCRIPTION OF THE INVENTION

Figure 1A:
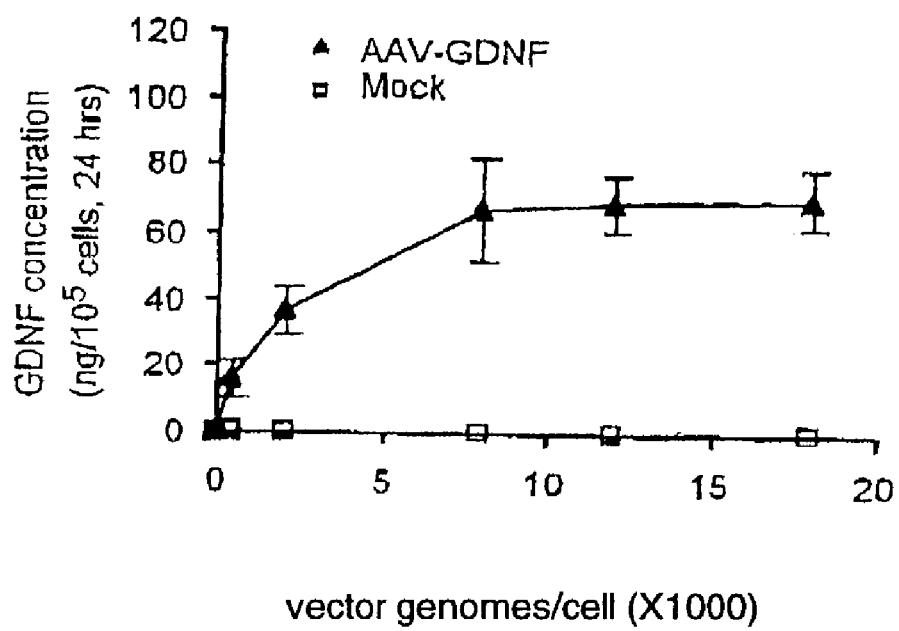
FIGS. 1A and 1B show the GDNF levels in conditioned medium and 293 cell lysate 48 post infection with AAV-GDNF-FLAG or AAV-LacZ as measured by ELISA.

The practice of the present invention will employ, unless otherwise indicated, conventional methods of virology, microbiology, molecular biology and recombinant DNA techniques within the skill of the art. Such techniques are explained fully in the literature. See, e.g., Sambrook et al. *Molecular Cloning: A Laboratory Manual* (Current Edition); *DNA Cloning: A Practical Approach*, Vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.); Freshney *Culture of Animal Cells, A Manual of Basic Technique* (Wiley-Liss, Third Edition); and Ausubel et al. (1991) *Current Protocols in Molecular Biology* (Wiley Interscience, NY).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

As used herein, the term "glial cell line-derived neurotrophic factor polypeptide" or "GDNF polypeptide" refers to a neurotrophic factor of any origin, which is substantially homologous and functionally equivalent to any of the various known GDNFs. Representative GDNFs for three mammalian species are shown in FIGS. 7, 8 and 9. The degree of homology between the rat (FIG. 8, SEQ ID NO:4) and human (FIG. 7, SEQ ID NO:2) protein is about 93% and all mammalian GDNFs have a similarly high degree of homology. Such GDNFs may exist as monomers, dimers or other multimers in their biologically active form. Thus, the term "GDNF polypeptide" as used herein encompasses active monomeric GDNFs, as well as active multimeric GDNFs, active glycosylated and non-glycosylated forms of GDNF and active truncated forms of the molecule.

By "functionally equivalent" as used herein, is meant a GDNF polypeptide that retains some or all of the biological properties regarding motoneurons, but not necessarily to the same degree, as a native GDNF molecule.

"Homology" refers to the percent similarity between two polynucleotide or two polypeptide moieties. Two polynucleotide, or two polypeptide sequences are "substantially homologous" to each other when the sequences exhibit at least about 50%, preferably at least about 75%, more preferably at least about 80%–85%, preferably at least about 90%, and most preferably at least about 95%–99% or more sequence similarity or sequence identity over a defined length of the molecules. As used herein, substantially homologous also refers to sequences showing complete identity to the specified polynucleotide or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis of similarity and identity, such as ALIGN, Dayhoff M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence similarity and identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent similarity of a particular nucleotide sequence to a reference sequence can be determined using the homology algorithm of Smith and Waterman with a default scoring table and a gap penalty of six nucleotide positions.

Another method of establishing percent similarity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence similarity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* supra; *Nucleic Acid Hybridization,* supra.

By "GDNF variant" is meant a biologically active derivative of the reference GDNF molecule, or a fragment of such a derivative, that retains desired activity, such as neurotrophic activity in the assays described herein. In general, the term "variant" refers to compounds having a native polypeptide sequence and structure with one or more amino acid additions, substitutions (generally conservative in nature) and/or deletions, relative to the native molecule, so long as the modifications do not destroy neurotrophic activity. Preferably, the variant has at least the same biological activity as the native molecule. Methods for making polynucleotides encoding for GDNF variants are known in the art and are described further below.

For GDNF deletion variants, deletions generally range from about 1 to 30 residues, more usually from about 1 to 10 residues, and typically from about 1 to 5 contiguous residues, or any integer within the stated ranges. N-terminal, C-terminal and internal deletions are contemplated. Deletions are generally introduced into regions of low homology with other TGF-β super family members in order to preserve maximum biological activity. Deletions are typically selected so as to preserve the tertiary structure of the GDNF protein product in the affected domain, e.g., cysteine crosslinking. Non-limiting examples of deletion variants include truncated GDNF protein products lacking from 1–40 N-terminal amino acids of GDNF, or variants lacking the C-terminal residue of GDNF, or combinations thereof.

For GDNF addition variants, amino acid sequence additions typically include N- and/or C-terminal fusions ranging in length from one residue to polypeptides containing a hundred or more residues, as well as internal additions of single or multiple amino acid residues. Internal additions generally range from about 1–10 residues, more typically from about 1–5 residues, and usually from about 1–3 amino acid residues, or any integer within the stated ranges. Examples of N-terminal addition variants include the fusion of a heterologous N-terminal signal sequence to the N-terminus of GDNF as well as fusions of amino acid sequences derived from the sequence of other neurotrophic factors.

GDNF substitution variants have at least one amino acid residue of the GDNF amino acid sequence removed and a different residue inserted in its place. Such substitution variants include allelic variants, which are characterized by naturally occurring nucleotide sequence changes in the species population that may or may not result in an amino acid change. Particularly preferred substitutions are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity.

For example, the GDNF molecule may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change using techniques well known in the art.

Specific mutations of the GDNF amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the GDNF amino acid sequence may be modified to add glycosylation sites.

Methods for identifying GDNF amino acid residues or regions for mutagenesis are well known in the art. One such method is known as "alanine scanning mutagenesis." See, e.g., Cunningham and Wells, *Science* (1989) 244:1081–1085. In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions are refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed GDNF variants are screened for the optimal combination of desired activity and degree of activity.

The sites of greatest interest for mutagenesis include sites where the amino acids found in GDNF proteins from various species are substantially different in terms of side-chain bulk, charge, and/or hydrophobicity. Other sites of interest are those in which particular residues of GDNF-like proteins, obtained from various species, are identical. Such positions are generally important for the biological activity of a protein. Initially, these sites are substituted in a relatively conservative manner. If such substitutions result in a change in biological activity, then more substantial changes (exemplary substitutions) are introduced, and/or other additions or deletions may be made, and the resulting products screened for activity.

Assays for GDNF activity are known in the art. For example, any of the various in vitro model systems, described more fully below, can be used as measures of GDNF activity.

By "motoneuron disorder" is meant a disease affecting a neuron with motor function, i.e., a neuron that conveys motor impulses. Such neurons are also termed "motor neruons." These neurons include, without limitation, alpha neurons of the anterior spinal cord that give rise to the alpha fibers which innervate the skeletal muscle fibers; beta neurons of the anterior spinal cord that give rise to the beta fibers which innervate the extrafusal and intrafusal muscle fibers; gamma neurons of the anterior spinal cord that give rise to the gamma (fusimotor) fibers which innervate the intrafusal fibers of the muscle spindal; heteronymous neurons that supply muscles other than those from which afferent impulses originate; homonymous neurons that supply muscles from which afferent impulses originate; lower peripheral neurons whose cell bodies lie in the ventral gray columns of the spinal cord and whose terminations are in skeletal muscles; peripheral neurons that receive impulses from internuerons; and upper neurons in the cerebral cortex that conduct impulses from the motor cortex to motor nuclei of the cerebral nerves or to the ventral gray columns of the spinal cord.

Nonlimiting examples of motoneuron disorders include the various amyotrophies such as hereditary amyotrophies including hereditary spinal muscular atrophy, acute infantile spinal muscular atrophy such as Werdnig-Hoffman disease, progressive muscular atrophy in children such as the proximal, distal type and bulbar types, spinal muscular atrophy of adolescent or adult onset including the proximal, scapuloperoneal, facioscapulohumeral and distal types, amyotrophic lateral sclerosis (ALS) and primary lateral sclerosis (PLS). Also included within the term is motoneuron injury.

By "skeletal muscle" is meant a striated muscle that is attached to bones and that typically crosses at least one joint. Scientifically, these muscles are often referred to as musculi skeleti.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By an "AAV vector" is meant a vector derived from an adeno-associated virus serotype, including without limitation, AAV-1, AAV-2, AAV-3, AAV-4, AAV-5, AAV-6, AAV-7 and AAV-8. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs and vectors that encode Rep and/or Cap expression products have been described. See, e.g., U.S. Pat. Nos. 6,001,650, 5,139,941 and 6,376,237, all incorporated herein by reference in their entireties; Samulski et al. (1989) *J. Virol.* 63:3822–3828; and McCarty et al. (1991) *J. Virol.* 65:2936–2945.

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid.

In particular, it has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol.* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions,* in I *CRC Handbook of Parvoviruses* (P. Tijssen ed., 1990)); E3 (Carter et al. (1983), supra); and E4 (Carter et al.(1983), supra; Carter (1995)). Although studies of the accessory functions provided by adenoviruses having mutations in the E1B coding region have produced conflicting results, Samulski et al., (1988) *J. Virol.* 62:206–210, recently reported that E1B55k is required for AAV virion production, while E1B19k is not. In addition, International Publication WO 97/17458 and Matshushita et al., (1998) *Gene Therapy* 5:938–945, describe accessory function vectors encoding various Ad genes.

Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

By "capable of supporting efficient rAAV virion production" is meant the ability of an accessory function vector or system to provide accessory functions that are sufficient to complement rAAV virion production in a particular host cell at a level substantially equivalent to or greater than that which could be obtained upon infection of the host cell with an adenovirus helper virus. Thus, the ability of an accessory function vector or system to support efficient rAAV virion production can be determined by comparing rAAV virion titers obtained using the accessory vector or system with titers obtained using infection with an infectious adenovirus. More particularly, an accessory function vector or system supports efficient rAAV virion production substantially equivalent to, or greater than, that obtained using an infectious adenovirus when the amount of virions obtained from an equivalent number of host cells is not more than about 200 fold less than the amount obtained using adenovirus infection, more preferably not more than about 100 fold less, and most preferably equal to, or greater than, the amount obtained using adenovirus infection.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus including an AAV protein shell, encapsidating a heterologous nucleotide sequence of interest which is flanked on both sides by AAV ITRs. A rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) *Gene* 13:197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

A "functional homologue," or a "functional equivalent" of a given AAV polypeptide includes molecules derived from the native polypeptide sequence, as well as recombinantly produced or chemically synthesized polypeptides which function in a manner similar to the reference AAV molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

A "functional homologue," or a "functional equivalent" of a given adenoviral nucleotide region includes similar regions derived from a heterologous adenovirus serotype, nucleotide regions derived from another virus or from a cellular source, as well as recombinantly produced or chemically synthesized polynucleotides which function in a manner similar to the reference nucleotide region to achieve a desired result. Thus, a functional homologue of an adenoviral VA RNA gene region or an adenoviral E2a gene region encompasses derivatives and analogues of such gene regions—including any single or multiple nucleotide base additions, substitutions and/or deletions occurring within the regions, so long as the homologue retains the ability to provide its inherent accessory function to support AAV virion production at levels detectable above background.

"Convection-enhanced delivery" refers to any non-manual delivery of agents. In the context of the present invention, examples of convection-enhanced delivery (CED) of AAV can be achieved by infusion pumps or by osmotic pumps. A more detailed description of CED is found below.

The terms "subject", "individual" or "patient" are used interchangeably herein and refer to a vertebrate, preferably a mammal. Mammals include, but are not limited to, murines, simians, humans, farm animals, sport animals and pets.

An "effective amount" is an amount sufficient to effect beneficial or desired results. An effective amount can be administered in one or more administrations, applications or dosages.

B. General Methods

The present invention is based on the surprising discovery that AAV vector-mediated GDNF gene delivery results in the durable and substantial expression of GDNF after a single intramuscular injection. As shown in the examples herein, substantial GDNF expression was achieved in a large number of myofibers and reached as high as nanogram levels in muscle and accumulated at the neuromuscular junctions. Expression persisted for at least 10 months. Moreover, the expressed GDNF was retrogradely transported through axons to corresponding spinal cord motoneurons. The transgene GDNF prevented degeneration of motoneurons, preserved the axons innervating the muscle, and inhibited muscle atrophy. Significantly, four-limb injection of AAV-GDNF in an amyotrophic lateral sclerosis (ALS) animal model postponed disease onset, delayed the progression of motor dysfunction, and prolonged the lifespan in treated animals. Consistent with these functional benefits, marked histopathologic amelioration such as reduced loss and atrophy of spinal cord motoneurons, more frequent intact neuromuscular connections, and reduced myofiber atrophy were also observed. Accordingly, delivery of GDNF via recombinant AAV virions provides a powerful and efficacious method for treating motoneuron disease, such as ALS.

The method described herein provides for the direct, in vivo injection of recombinant AAV virions into muscle tissue, preferably skeletal muscle, e.g., by intramuscular injection, as well as for the in vitro transduction of muscle cells which can subsequently be introduced into a subject for treatment. The methods described herein can be used to treat a number of motoneuron diseases such as any of the various amyotrophies such as hereditary amyotrophies including hereditary spinal muscular atrophy, acute infantile spinal muscular atrophy such as Werdnig-Hoffman disease, progressive muscular atrophy in children such as the proximal, distal type and bulbar types, spinal muscular atrophy of adolescent or adult onset including the proximal, scapuloperoneal, facioscapulohumeral and distal types, amyotrophic lateral sclerosis (ALS) and primary lateral sclerosis (PLS).

As explained above, GDNF is a protein that may be identified in or obtained from glial cells and that exhibits neurotrophic activity. GDNF is an approximately 39 kD glycosylated protein that exists as a homodimer in its native form. GDNF is initially translated as a pre-pro-GDNF polypeptide and proteolytic processing of the signal sequence and the "pro" portion of the molecule result in production of a mature form of GDNF. In humans and rodents, a single gene gives rise to alternatively spliced forms. See, e.g., U.S. Pat. No. 6,362,319, incorporated herein by reference in its entirety. Both forms contain a consensus signal peptide sequence and a consensus sequence for proteolytic processing. Proteolytic cleavage yields identical mature 134 amino acid residue forms. Thus, GDNF polynucleotides for use in the present AAV vectors may encode either or both of these forms, may encode the entire pre-pro-molecule, the pre-molecule, the pro-molecule, the mature GDNF polypeptide, or biologically active variants of these forms, as defined above.

A number of GDNF polynucleotide and amino acid sequences are known. Three representative mammalian GDNF sequences are depicted in FIGS. 7, 8 and 9 herein. In particular, a human GDNF nucleotide and amino acid sequence is shown in FIG. 7 (SEQ ID NOS:1 and 2). A rat GDNF nucleotide and amino acid sequence is shown in FIG. 8 (SEQ ID NOS:3 and 4) and a mouse GDNF nucleotide and amino acid sequence is shown in FIG. 9 (SEQ ID NOS:6 and 7). The degree of homology between the rat and human proteins is about 93% and all mammalian GDNFs have a similarly high degree of homology. Additional GDNF nucleotide and amino acid sequences are known in the art. See, e.g., U.S. Pat. Nos. 6,221,376 and 6,363,319, incorporated herein by reference in their entireties, and Lin et al., *Science* (1993) 260:1130–1132 for rat and human sequences, as well as NCBI accession numbers AY052832, AJ001896, AF053748, AF063586 and L19063 for human sequences; NCBI accession numbers AF184922, AF497634, X92495, NM019139 for rat sequences; NCBI accession number AF516767 for a giant panda sequence; NCBI accession numbers XM122804, NM010275, D88351S1, D49921, U36449, U37459, U66195 for mouse sequences; NCBI accession number AF469665 for a Nipponia nippon sequence; NCBI accession number AF106678 for a Macaca mulatta sequence; and NCBI accession numbers NM131732 and AF329853 for zebrafish sequences. As explained above, any of these sequences, as well as variants thereof, such as sequences substantially homologous and functionally equivalent to these sequences, will find use in the present methods.

The efficacy of AAV-delivered GDNF polynucleotides can be tested in any of a number of animal models of the above diseases, known in the art. For example, scientifically accepted and widely used animal models for the study of motoneuron disorders such as ALS are transgenic mice with an ALS-linked mutant Cu/Zn superoxide dismutase (SOD1) gene (mSOD1G93A and/or mSOD1G37R). These mice develop a dominantly inherited adult-onset paralytic disorder with many of the clinical and pathological features of familial ALS. See, e.g., Gurney et al., *Science* (1994) 264:1772–1775; Nagano et al., *Life Sci* (2002) 72:541–548. Other animal models include two naturally occurring murine models (progressive motor neuronopathy (pmn) and wobbler). See, e.g., Haegggeli and Kato, *Neurosci. Lett.* (2002) 335:39–43, for descriptions of these mouse models. For a review of various animal models for use in studying motoneuron diseases such as ALS, see, e.g., Jankowsky et al., Curr Neurol *Neurosci. Rep.* (2002) 2:457–464; Elliott, J. L., *Neurobiol. Dis.* (1999) 6:310–20; and Borchelt et al., *Brain Pathol.* (1998) 8:735–757.

Additionally, several in vitro model systems are known which use cells, tissue culture and histological methods for studying motoneuron disease. For example, a rat spinal cord organotypic slice subjected to glutamate excitotoxicity is useful as a model system to test the effectiveness of neurotrophic factors in preventing motor neuron degeneration. Corse et al., *Neurobiol. Dis.* (1999) 6:335–346. For a discussion of in vitro systems for use in studying ALS, see, e.g., Bar, P. R., *Eur. J. Pharmacol.* (2000) 405:285–295; Silani et al., *J. Neurol.* (2000) 247 Suppl 1:128–36; Martin et al., *Int. J. Mol. Med.* (2000) 5:3–13.

Animal models of other neurodegenerative diseases have been described and are useful for evaluating the therapeutic efficacy of AAV-delivered GDNF polynucleotides in the treatment of motoneuron disorders in addition to ALS. See, for example, Katsuno et al., *Neuron* (2002) 35:843–854 for a transgenic mouse model for evaluating spinal and bulbar muscular atrophy (SBMA); Ford et al., *Microb. Pathog.* (2002) 33:97–107 for a description of animal models for human paralytic poliomyelitis.

Recombinant AAV virions comprising GDNF coding sequences may be produced using a variety of art-recognized techniques described more fully below. Wild-type AAV and helper viruses may be used to provide the necessary replicative functions for producing rAAV virions (see, e.g., U.S. Pat. No. 5,139,941, incorporated herein by reference in its entirety). Alternatively, a plasmid, containing helper function genes, in combination with infection by one of the well-known helper viruses can be used as the source of replicative functions (see e.g., U.S. Pat. No. 5,622,856 and U.S. Pat. No. 5,139,941, both incorporated herein by reference in their entireties). Similarly, a plasmid, containing accessory function genes can be used in combination with infection by wild-type AAV, to provide the necessary replicative functions. These three approaches, when used in combination with a rAAV vector, are each sufficient to produce rAAV virions. Other approaches, well known in the art, can also be employed by the skilled artisan to produce rAAV virions.

In a preferred embodiment of the present invention, a triple transfection method (described in detail in U.S. Pat. No. 6,001,650, incorporated by reference herein in its entirety) is used to produce rAAV virions because this method does not require the use of an infectious helper virus, enabling rAAV virions to be produced without any detectable helper virus present. This is accomplished by use of three vectors for rAAV virion production: an AAV helper function vector, an accessory function vector, and a rAAV expression vector. One of skill in the art will appreciate, however, that the nucleic acid sequences encoded by these vectors can be provided on two or more vectors in various combinations.

As explained herein, the AAV helper function vector encodes the "AAV helper function" sequences (i.e., rep and cap), which function in trans for productive AAV replication and encapsidation. Preferably, the AAV helper function vector supports efficient AAV vector production without generating any detectable wt AAV virions (i.e., AAV virions containing functional rep and cap genes). An example of such a vector, pHLP19 is described in U.S. Pat. No. 6,001,650, incorporated herein by reference in its entirety. The rep and cap genes of the AAV helper function vector can be derived from any of the known AAV serotypes, as explained above. For example, the AAV helper function vector may have a rep gene derived from AAV-2 and a cap gene derived from AAV-6; one of skill in the art will recognize that other rep and cap gene combinations are possible, the defining feature being the ability to support rAAV virion production.

The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the well-known helper viruses such as adenovirus, herpesvirus (other than herpes simplex virus type-1), and vaccinia virus. In a preferred embodiment, the accessory function plasmid pLadeno5 is used (details regarding pLadeno5 are described in U.S. Pat. No. 6,004,797, incorporated herein by reference in its entirety). This plasmid provides a complete set of adenovirus accessory functions for AAV vector production, but lacks the components necessary to form replication-competent adenovirus.

In order to further an understanding of the invention, a more detailed discussion is provided below regarding recombinant AAV expression vectors, AAV helper and accessory functions, compositions comprising AAV virions, as well as delivery of virions.

Recombinant AAV Expression Vectors

Recombinant AAV (rAAV) expression vectors are constructed using known techniques to at least provide as operatively linked components in the direction of transcription, control elements including a transcriptional initiation region, the GDNF polynucleotide of interest and a transcriptional termination region. The control elements are selected to be functional in a mammalian muscle cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793–801; Bems, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-6, AAV-7 and AAV-8, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable GDNF polynucleotide molecules for use in AAV vectors will be less than about 5 kilobases (kb) in size. The selected polynucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, neuron-specific enolase promoter, a GFAP promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

For purposes of the present invention, muscle-specific and inducible promoters, enhancers and the like, will be of particular use. Such control elements include, but are not limited to, those derived from the actin and myosin gene families, such as from the myoD gene family (Weintraub et al. (1991) *Science* 251:761–766); the myocyte-specific enhancer binding factor MEF-2 (Cserjesi and Olson (1991) *Mol. Cell Biol.* 11:4854–4862); control elements derived from the human skeletal actin gene (Muscat et al. (1987) *Mol. Cell Biol.* 7:4089–4099) and the cardiac actin gene; muscle creatine kinase sequence elements (Johnson et al. (1989) *Mol Cell Biol.* 9:3393–3399) and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors (Semenza et al. (1991) *Proc. Natl. Acad. Sci. USA* 88:5680–5684; Semenza et al. *J. Biol. Chem.* 269:23757–23763); steroid-inducible elements and promoters, such as the glucocorticoid response element (GRE) (Mader and White (1993) *Proc. Natl. Acad. Sci. USA* 90:5603–5607); the fusion consensus element for RU486 induction; elements that provide for tetracycline regulated gene expression (Dhawan et al. (1995) *Somat. Cell. Mol. Genet.* 21:233–240; Shockett et al. (1995) *Proc. Natl. Acad. Sci. USA* 92:6522–6526); and inducible, synthetic humanized promoters (Rivera et al. (1996) *Nature Med.* 2:1028–1032). These and other regulatory elements can be tested for potential in vivo efficacy using the in vitro myoblast model, which mimics quiescent in vivo muscle physiology.

The AAV expression vector which harbors the GDNF polynucleotide molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines* 90 (Cold Spring Harbor Laboratory Press); Carter (1992) *Current Opinion in Biotechnology* 3:533–539; Muzyczka (1992) *Current Topics in Microbiol. and Immu-* nol. 158:97–129; Kotin (1994) *Human Gene Therapy* 5:793–801; Shelling and Smith (1994) *Gene Therapy* 1:165–169; and Zhou et al. (1994) *J. Exp. Med.* 179: 1867–1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM $MgCl_2$, 10 mM DTT, 33 µg/ml BSA, 10 mM–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 µg/ml total DNA concentrations (5–100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian muscle cells can be used. The complete chimeric sequence is assembled from overlapping oligonucleotides prepared by standard methods. See, e.g., Edge (1981) *Nature* 292:756; Nambair et al. (1984) *Science* 223:1299; Jay et al. (1984) *J. Biol. Chem.* (1984) 259:6311.

For the purposes of the invention, suitable host cells for producing rAAV virions from the AAV expression vectors include microorganisms, yeast cells, insect cells, and mammalian cells, that can be, or have been, used as recipients of a heterologous DNA molecule and that are capable of growth in suspension culture. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97–129; and Kotin, R. M. (1994) *Human Gene Therapy* 5:793–801. Suitable homologues of the AAV rep coding region include the human herpesvirus 6 (HHV-6) rep gene which is also known to mediate AAV-2 DNA replication (Thomson et al. (1994) *Virology* 204:304–311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) *J. Virol.* 65:2936–2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241–247; McPherson et al. (1985) *Virology* 147:217–222; Schlehofer et al. (1986) *Virology* 152:110–117.

Alternatively, accessory functions can be provided using an accessory function vector as defined above. See, e.g., U.S. Pat. No. 6,004,797 and International Publication No. WO 01/83797, incorporated herein by reference in its entirety. Nucleic acid sequences providing the accessory functions can be obtained from natural sources, such as from the genome of an adenovirus particle, or constructed using recombinant or synthetic methods known in the art. As explained above, it has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 104:502); E2A (Handa et al., (1975) *J. Gen. Virol.* 29:239; Strauss et al., (1976) *J. Virol.* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions,* in I *CRC Handbook of Parvoviruses* (P. Tijssen ed., 1990)); E3 (Carter et al. (1983), supra); and E4 (Carter et al.(1983), supra; Carter (1995)). Although studies of the accessory functions provided by adenoviruses having mutations in the E1B coding region have produced conflicting results, Samulski et al., (1988) *J. Virol.* 62:206–210, recently reported that E1B55k is required for AAV virion production, while E1B19k is not. In addition, International Publication WO 97/17458 and Matshushita et al., (1998) *Gene Therapy* 5:938–945, describe accessory function vectors encoding various Ad genes.

Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions containing the GDNF nucleotide sequence of interest can then be used for gene delivery using the techniques described below.

Compositions

Compositions will comprise sufficient genetic material to produce a therapeutically effective amount of the GDNF of interest, i.e., an amount sufficient to reduce or ameliorate symptoms of the disease state in question or an amount sufficient to confer the desired benefit. The compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

One particularly useful formulation comprises recombinant AAV virions in combination with one or more dihydric or polyhydric alcohols, and, optionally, a detergent, such as a sorbitan ester. See, for example, International Publication No. WO 00/32233.

As is apparent to those skilled in the art in view of the teachings of this specification, an effective amount of viral vector which must be added can be empirically determined. Representative doses are detailed below. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene can be expressed by the delivered recombinant virion. Alternatively, separate vectors, each expressing one or more different transgenes, can also be delivered as described herein. Furthermore, it is also intended that the viral vectors delivered by the methods of the present invention be combined with other suitable compositions and therapies. Where the transgene is under the control of an inducible promoter, certain systemically delivered compounds such as muristerone, ponasteron, tetracyline or aufin may be administered in order to regulate expression of the transgene.

Delivery of AAV Virions

Recombinant AAV virions may be introduced into muscle cells using either in vivo or in vitro (also termed ex vivo) transduction techniques. If transduced in vitro, the desired recipient cell, preferably a skeletal muscle cell, will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with cells to be transduced in appropriate media, and those cells harboring the DNA of interest can be screened using conventional techniques such as Southern blots and/or PCR, or by using selectable markers. Transduced cells can then be formulated into pharmaceutical compositions, as described above, and the composition introduced into the subject by various techniques as described below, in one or more doses.

Recombinant AAV virions or cells transduced in vitro may be delivered directly to muscle by injection with a needle, catheter or related device, using techniques known in the art. For in vivo delivery, the rAAV virions will be formulated into pharmaceutical compositions and one or more dosages may be administered directly in the indicated manner. A therapeutically effective dose will include on the order of from about $10^8$/kg to $10^{16}$/kg of the rAAV virions, more preferably $10^{10}$/kg to $10^{14}$/kg, and even more preferably about $10^{11}$/kg to $10^{13}$/kg of the rAAV virions (or viral genomes, also termed "vg"), or any value within these ranges.

One mode of administration of recombinant AAV virions uses a convection-enhanced delivery (CED) system. In this way, recombinant virions can be delivered to many cells over large areas of muscle. Moreover, the delivered vectors efficiently express transgenes in muscle cells. Any convection-enhanced delivery device may be appropriate for delivery of viral vectors. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.). Typically, a viral vector is delivered via CED devices as follows. A catheter, cannula or other injection device is inserted into appropriate muscle tissue in the chosen subject, such as skeletal muscle. For a detailed description regarding CED delivery, see U.S. Pat. No. 6,309,634, incorporated herein by reference in its entirety.

Other modes of administration that will find particular use with muscles use histamine or isolated limb perfusion (a technique where the vascular supply to a limb is isolated from systemic circulation before infusion of the composition in question) for increasing vector spread in the muscle, all well known techniques in the art. See, e.g., Schaadt et al., *J. Extra Corpor. Technol.* (2002) 34:130–143; Lejeune et al., *Surg. Oncol. Clin. N. Am.* (2001) 10:821–832; Fraser et al., *AORN J* (1999) 70:642–647, 649, 651–653.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Construction of Recombinant AAV Vectors

In order to distinguish AAV-delivered GDNF from its endogenous counterpart, an AAV vector was constructed encoding a recombinant fusion GDNF protein, tagged with the FLAG peptide (AAV-GDNF-FLAG), for recognition by a specific antibody to the FLAG epitope. Briefly, AAV vector plasmid pAAV-GDNF-FLAG was derived from a previously described pAAV-GDNF plasmid (Fan et al., *Neurosci. Lett.* (1998) 248:61–64). This plasmid contains the mouse GDNF cDNA (Matsushita et al., *Gene* (1997) 203:149–157) tagged by the FLAG sequence (DYKD-DDDK (SEQ ID NO:5) at the carboxyl terminus under the human cytomegalovirus (CMV) immediate-early promoter, with human growth hormone first intron and simian virus 40 (SV40) polyadenylation signal sequence between the inverted terminal repeats (ITR) of the AAV-2 genome.

AAV vector plasmid pAAV-LacZ, auxiliary plasmid pHLP19 and pladenol have previously been described (Fan et al., *Neurosci. Lett.* (1998) 248:61–64; Shen et al., *Hum. Gene Ther.* (2000) 11:1509–1519). Pladeno5 is described in U.S. Pat. No. 6,004,797. Subconfluent human 293 cells were transiently transfected with vector plasmid and helper plasmid using the calcium phosphate co-precipitation method. Seventy-two hours after transfection, cells were harvested and lysed by freeze and thaw cycles. AAV vectors (AAV-GDNF-FLAG and AAV-LacZ) were purified using two sequential continuous CsCl gradients, as described previously (Matsushita, et al, *Gene Therapy* (1998) 5:938–945). The final particle titer of the AAV-GDNF-FLAG was $1.6 \times 10^3$ vector genome copies/ml and AAV-LacZ was $2.1 \times 10^{13}$ vector genome copies/ml, as estimated by quantitative DNA dot-blot hybridization analysis.

EXAMPLE 2

In vitro Expression of AAV-GDNF-FLAG

To detect the in vitro expression of GDNF-FLAG fusion protein, human embryonic kidney (HEK) 293 cells (readily available through, e.g., the American Type Culture Collection under Accession Number ATCC CRL1573) were seeded on 35 mm-diameter dishes and allowed to proliferate overnight in complete medium. Cells were transduced with AAV-GDNF-FLAG or AAV-LacZ ($0.5–18 \times 10^3$ vector genome copies/cell) in medium supplied with 2% fetal bovine serum. 48 hours after transduction, conditioned medium (CM) and cell lysates were collected.

GDNF levels in CM and 293 cell lysate were measured by ELISA (GDNF $E_{max}$ ImmunoAssay System, Promega). For the detection in cell lysate, cells were homogenized in lysis buffer ($137 \times 10^{-3}$ mol/L NaCl, $20 \times 10^{-3}$ mol/L Tris [pH 8.0], 1% NP40, 10% glycerol, supplied by Protease Inhibitor Cocktail Tablets Complete Mini [Roche]), ultrasonicated and centrifuged at 4° C. The supernatants were acidified and then neutralized to pH 7.4 before assay. Acidification has been reported to enhance detection of neurotrophic factors (Okragly et al., *Exp. Neurol.* (1997) 145:592–596). Triplicate samples were processed in 96-well plates according to the detailed protocol provided by Promega. Briefly, plates were coated with anti-GDNF monoclonal antibody, blocked and incubated with GDNF standards or samples. Plates were then incubated sequentially with chicken anti-human GDNF polyclonal antibody, anti-chicken 1gY-peroxidase conjugate, followed by peroxidase substrate and tetramethylbenzidine solution for color development. The reaction was stopped with 1N HCl and the absorbance was read at 450 nm. Levels of GDNF were expressed as pg/mg tissue. The assay sensitivity ranged from 16 pg/ml to 1,000 pg/ml.

Figure 1B:
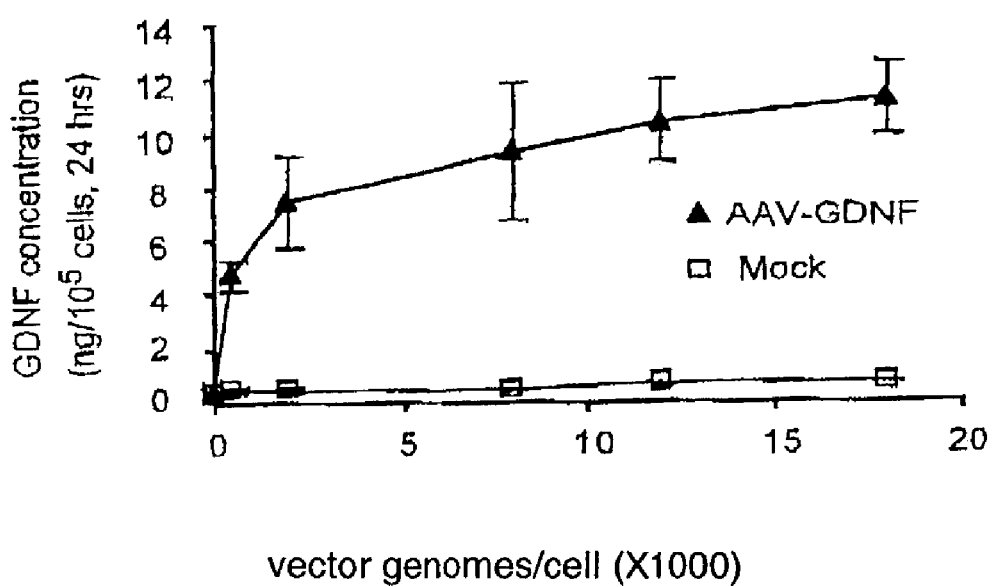

ELISA analysis showed high levels of GDNF expression and secretion in AAV-GDNF-FLAG-transduced cells (FIGS. 1A and 1B). As expected, GDNF levels in the CM were much higher than the cell lysate, indicating that the GDNF could be secreted by cells. Moreover, at the range detected, the amount of GDNF in CM and cell lysates showed a vector genome copies per cell/dose-dependent increase. In the non-transduced or AAV-LacZ-transduced 293 cells, GDNF levels were much lower, barely at the detection limit of the ELISA analysis.

EXAMPLE 3

In vivo Expression of GDNF in Injected Gastrocnemius Muscles

Male C57BL/6J mice (7 weeks old) were injected with either AAV-GDNF-FLAG (n=32) or AAV-LacZ (n=21) virions in the left hindlimb gastrocnemius muscles ($2 \times 10^{10}$ viral genome copies in 24 μl PBS/3 sites) percutaneously using a microsyringe connected to a 27-gauge needle. As a sham control, the right gastrocnemius muscle was injected with same volume of PBS. No morbidity or morality was observed in nice during the experimental period. At the indicated time (see FIG. 2), gastrocnemius muscles were dissected, rapidly frozen in liquid nitrogen-cooled isopentane and stored at –80° C. for ELISA analysis or Cryostat sectioning. Mice were then perfused with ice-cold PBS followed by 4% paraphormaldehyde (PFA). Spinal cord was dissected, post-fixed for 4 hours in 4% PFA and cryoprotected by soaking sequentially in 10%, 20% and 30% sucrose at 4° C. overnight. Serial transverse Cryostat sections of frozen muscle tissue (10 μm) were thawed mounted in slides, coated with gelatin, and completely dried before storing at –80° C. Serial transverse sections of lumbar spinal cord were cut on freezing microtome at 30 μm thickness, and stored in PBS at 4° C.

GDNF ELISAs were performed as described above. For β-galactosidase (β-Gal) histochemistry, muscle sections were fixed and stained for 4–6 hours with β-Gal staining solution (500 μg/ml X-Gal, 5 mM potassium hexacycanoferrate (III), 5 mM potassium hexacyanoferrate (II), and 2 mM magnesium chloride in PBS) at 37° C. Spinal cord samples were stained as free-floating sections and mounted in gelatin-coated slices and dried. Sections were counterstained with eosin for detection. Immunohistochemistry staining with anti-FLAG antibody was performed on gastrocnemius muscle cryostat sections for the purpose of distinguishing transgene GDNF from endogenous GDNF. Muscle sections were fixed and treated with 0.3% $H_2O_2$, then sequentially incubated with anti-FLAG antibody (1:1000, rabbit polyclonal anti-FLAG antibody, Sigma) overnight at 4° C. and a biotinylated secondary antibody to rabbit IgG (1:400) for two hours, and visualized using the avidin-biotinylated peroxidase complex procedure (Vectastain ABC lots. Vector Laboratories Inc. Burlingame, Calif.), using 3,3-diaminobenzidine (DAB) as a chromogen. For double immunofluorescence staining, muscle and spinal cord sections were stained with the Mouse-on-Mouse kit (M.O.M kit) (Vector Laboratories, Burlingame, Calif.), according to the manufacturer's protocol. Primary antibodies used for muscle sections were mouse anti-FLAG $M_2$ antibody (1:500, Sigma) and rabbit anti-GDNF antibody (1:1000, Santa Cruz). For spinal cord sections antibodies were rabbit anti-FLAG antibody (1:1000, Sigma) and mouse anti-NeuN antibody (1:200, Chemicon). Sections were then incubated with rhodamine or FITC-conjugated corresponding secondary antibodies for detection. For double immunofluorescent staining of muscle sections with anti-FLAG antibody and α-bungarotoxin, sections were incubated with rabbit anti-FLAG antibody first, followed by incubation with FITC-conjugated anti-rabbit secondary antibody and tetramethyl-rhodamine conjugated α-bungarotoxin molecular probe (1:400, Molecular Probes, Inc., Eugene, USA). α-Bungarotoxin is a peptide extracted from *Bungarus multicinctus*, which specifically binds with high affinity to the α-subunit of the nicotinic AchR at the postsynaptic membrane of neuromuscular junctions. Immunofluorescent stained sections were viewed and photographs were captured with a confocal laser scanning microscope (TCS NT; Leica, Heidelberg, Germany).

Figure 2:
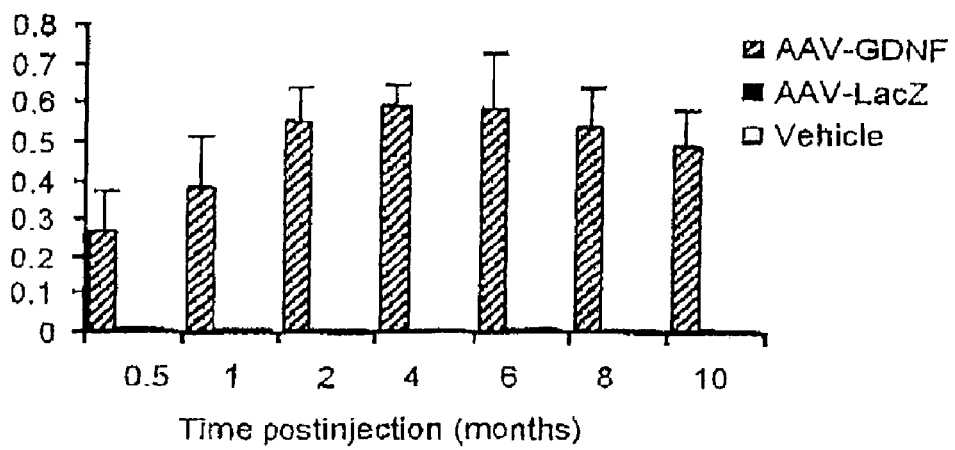
FIG. 2 shows GDNF levels in gastrocnemius muscle of injected mice at various time points post-injection.

ELISA Detection of GDNF levels in AAV-GDNF-FLAG-injected gastrocnemius muscles showed that GDNF expression could be detected 14 days postinjection, gradually increased over the first 2 months and remained stable without significant diminution over 6 months, then showed slight reduction from 8 months postinjection (FIG. 2). The substantial expression persisted at least 10 months, the last time point tested. The gastrocnemius muscles injected with AAV-LacZ vector or PBS exhibited very low levels of GDNF.

In gastrocnemius muscles injected with AAV-GDNF-FLAG, substantial and sustained immunoreactive signals for FLAG were detected in a large number of myofibers, from 2 weeks to 10 months postinjection. Double-immunofluorescent staining with anti-GDNF and anti-FLAG antibodies showed co-localization of GDNF and FLAG immunoreactivity, confirming the presence of a GDNF-FLAG fusion protein. Intense immunoreactivity was concentrated in the vicinity of the sarcolemmas, suggesting its effective secretion by myofibers in vivo. In AAV-LacZ- or PBS-injected muscles, only very weak signals of GDNF could be detected in the vicinity of sarcolemmas, while no immunosignals of FLAG were seen. This is in agreement with ELISA results and indicated that the GDNF detected by ELISA in AAV-LacZ- or PBS-injected muscles was endogenous GDNF.

To summarize, substantial transgene GDNF was expressed in vivo and expression reached as high as nanogram levels from each gastrocnemius muscle and persisted for as long as at least 10 months. A slight diminution was observed beginning at 8 months postinjection and is consistent with published results of other groups (Verma and Somia, *Nature* (1997) 389:239–242) as well as our unpublished results in the striatum. Without being bound by a particular theory, this diminution in expression may be due to promoter shut-off, degradation of the vector genome, and/or turnover of the transduced myofibers (Verma and Somia, *Nature* (1997) 389:239–242; Rabinowitz and Samulski, *Curr. Opin. Biotechnol.* (1998) 2:470–475).

According to the neurotrophic theory, neurites connect with their targets to gain access to target-derived neurotrophic factors for neuron survival. In particular, neurotrophic factor is synthesized and released by the targets of neurotrophic factor-dependent axons, where it is bound by receptors on axon terminals, taken up, and retrogradely transported to the cell body (DeStefano, P. S., *Exp. Neurol.* (1993) 124:56–69). To determine whether transgene-delivered GDNF-FLAG also followed the neurotrophic theory of GDNF, double-immunofluorescent staining with anti-FLAG antibody and rhodamine-conjugated α-bungarotoxin was performed on gastrocnemius muscle sections. Confocal microscopy showed co-localization of more intense immunoreactivity for FLAG with signals of α-bungarotoxin, indicating the concentration of transgene GDNF-FLAG fusion protein to regions of neuromuscular junctions (NMJs). The accumulation of transgene GDNF at NMJs suggested that, consistent with the neurotrophic theory, NMJ is a site for transgene GDNF uptake by nerve terminals as a target-derived neurotrophic factor. In AAV-LacZ- or PBS-injected sections, only rhodamine signals indicating the NMJs could be detected, with no FLAG immunoreactive signal. In the gastrocnemius muscles injected with AAV-LacZ vector, β-gal activity was detected in a large number of the myofibers but in an expression pattern totally different than the transgene GDNF. The expression lasted from 2 weeks to 10 months postinjection. These results show that a single injection of AAV-GDNF-FLAG in the gastrocnemius muscle is able to mediate durable and substantial expression of transgene GDNF, which was distributed mainly in the vicinity of the sarcolemmas and accumulated at the NMJs.

The distribution of transgene GDNF-FLAG fusion protein in muscle detected by anti-FLAG antibody is similar to that of endogenous GDNF observed in normal human muscles (Suzuki et al., *J. Comp. Neurol.* (1998) 402:303–312).

As a target-derived neurotrophic factor, endogenous GDNF produced by skeletal muscle functions via retrograde axonal transport from the target muscle tissue to motoneuronal cell bodies in the spinal cord (Mitsumoto, H., *Muscle Nerve* (1999) 22:1000–1021; Leitner et al., *J. Neurosci.* (1999) 19:9322–9331). Receptor-mediated retrograde transport of GDNF has been described in motoneurons of rats (Leitner et al., *J. Neurosci.* (1999) 19:9322–9331). Although the physiological significance of retrograde transport is not completely understood, it is thought to be of critical importance in axon-target communication and neuronal viability, probably reflecting the conveyance of a signal transduction complex (Neet and Capenot, *Cell. Mol. Life Sci.* (2001) 58:1221–1235).

In order to determine whether transgene GDNF-FLAG fusion protein could also be retrogradely transported from muscle to spinal cord motoneurons, double-immunostaining with anti-FLAG and anti-NeuN (a specific marker of neuron) antibodies, was performed on lumber 4 to 6 spinal cord sections corresponding with the innervation of gastrocnemius muscles. FLAG immunoreactivity was detected in large size NeuN-positive cells of ventral horn ipsilateral to the AAV-GDNF-FLAG injected side. Their large size (with diameters >20 μm), ventral horn distribution and NeuN-positive characteristics suggested that these FLAG immunoreactive cells were α-motoneurons. As anti-FLAG antibody was used which excluded the interference from endogenous GDNF, this evidenced the existence of transgene GDNF-FLAG fusion protein in the motoneurons. In contrast, no FLAG staining was detected in the ventral horn of the contralateral side as well as in both ventral horns of AAV-LacZ- or PBS-injected mice. No β-galactosidase signal was detected in the corresponding ventral horns of spinal cord sections from AAV-LacZ-injected mice, in spite of the wide distribution β-galactosidase signals in the muscles.

Thus, transgene GDNF was successfully detected in the ipsilateral ventral horn motoneurons of the spinal cord, following its detection in gastrocnemius muscle after AAV-GDNF-FLAG injection. The transgene GDNF might have been delivered to the spinal cord via three different avenues: systemic delivery, retrograde transport of AAV vectors or retrograde transport of the fusion protein itself. The restricted distribution and ipsilateral presentation of transgenic GDNF in motoneurons as well as its inability to pass through the blood-brain barrier excludes the possibility of systematic delivery to the spinal cord. Additionally, β-galactosidase signal was not detected in spinal cord motoneurons of AAV-LacZ injected mice, indicating that the AAV vector itself was not delivered by retrograde transport. This evidences that the transgene GDNF-FLAG fusion protein detected in the spinal cord was derived from the retrograde axonal transport of this protein from muscles to the motoneurons, but not the AAV vector per se. This is consistent with previous reports (Kordower et al., *Science* (2000) 290:767–773; Wang et al., *Gene Ther.* (2002) 2:381–389). Retrograde axonal transport of adenovirus vectors or lentiviral vectors has been reported (Ghadge et al., *Gene Ther.* (1995) 2:132–137; Haase et al., *Nat. Med.* (1997) 3:429–436; Desmaris et al., *Mol. Ther.* (2001) 4:149–156), but until the present discovery, no positive evidence supporting the massive retrograde axonal transport of AAV-delivered gene products has ever been reported.

In conclusion, the above examples demonstrate that AAV-GDNF-FLAG injection to the gastrocnemius muscle supplies a continuous source of transgene GDNF at the nerve terminals and constitutes a safe, durable and specific method to deliver GDNF to the motoneuronal bodies in the spinal cord. This, taken together with previous results that the transgenic GDNF-FLAG fusion protein retains intact bioactivity as GDNF, shows the utility of AAV-mediated gene therapy for the treatment of motor neuron disease.

EXAMPLE 4

GDNF Transgene Expression in Muscles of ALS Mice

In order to determine whether AAV-mediated delivery of GDNF would be useful for treating a motoneuron disease, such as ALS, the following study was conducted.

A. Materials and Methods

Administration of Recombinant AAV virions. Male transgenic mice with the G93A human SOD1 mutation (SOD1G93A) were obtained from The Jackson Laboratory (Bar Harbor, Me.). pAAV-GDNF-FLAG, pAAV-LacZ, auxiliary plasmid pHLP19 and pladenol were as described above. AAV vectors were produced in human embryonic kidney (HEK) 293 cells by triple transfection of vector plasmid and helper plasmids listed above as described previously (Wang et al., *Gene Ther.* (2002) 2:381–389). In brief, subconfluent 293 cells were transiently transfected using the calcium phosphate method. 72 hours after transfection, the cells were collected and subjected to three cycles of freeze-thaw lysis (alternating between dry-ice-ethanol and 37° C. baths). AAV vectors were purified by two sequential continuous cesium chloride density gradients and estimated for final particle titer by quantitative DNA dot-blot hybridization.

Before administration, AAV vectors were diluted in PBS to $1\times10^{11}$ genome copies/100 μl. At 9 weeks of age, ALS mice were randomly assigned to one treatment group that was injected with AAV-GDNF vector (n=12) or one of two control groups that were injected with AAV-LacZ vector (n=6) and the vehicle (n=5), respectively, into four limbs (gastrocnemius and triceps brachii muscles). The dosage was 30 μl for gastrocnemius and 20 μl for triceps brachii muscles. Because mice injected with AAV-LacZ vector and the vehicle were indistinguishable with regard to all variables tested during the experimental period, the two groups were considered as one control group for analysis. In another subgroup (n=7), all of the mice had AAV-GDNF vector injected into the muscles of the left forelimbs and hindlimbs and AAV-LacZ vector into those of the right ones.

Behavioral testing and mortality. Mice were first given three days to become acquainted with the rotarod apparatus (Rota-Rod/7650; Ugo Basile, Comerio, Italy) before the test. For detection, mice were placed on the rotating rod at the speeds of 5, 10, and 20 rpm, and the time each mouse remained on the rod was registered automatically. The onset of disease was defined as the time when the mouse could not remain on the rotarod for 7 min at a speed of 20 rpm, as described previously (Li et al., Science (2000) 288:335–339). If the mouse remained on the rod for >7 min, the test was completed and scored as 7 min. Mice were tested every two days until they could no longer perform the task. Mortality was scored as the age of death when the mouse was unable to right itself within 30 sec when placed on its back in a supine position (Li et al., Science (2000) 288:335–339).

Tissue preparation. One week before being sacrificed, mice were bilaterally injected with neural tracer cholera toxin subunit B (CTB) (0.1% in distilled $H_2O$, 3 μl; List Biologic, Campbell, Calif.) into gastrocnemius muscles to selectively label motoneurons that retained axons innervating the treated muscles. At the indicated times, gastrocnemius muscles were dissected out, weighed, rapidly frozen in liquid nitrogen-cooled isopentane, and then stored at –80° C. for immunohistochemistry or GDNF ELISA analysis. After dissecting out the muscles, the mice were perfused with ice-cold PBS, followed by 4% paraformaldehyde (PFA). The spinal cord was dissected out, postfixed for 4 hr in 4% PFA, and then cryoprotected sequentially in sucrose.

GDNF ELISA. To determine muscle GDNF levels, tissues were homogenized at a w/v ratio of 100 mg/ml in lysis buffer ($137\times10^{-3}$ mol/l NaCl, $20\times10^{-3}$ mol/l Tris, pH 8.0, 1% NP-40, and 10% glycerol) containing protease and phosphatase inhibitors, ultrasonicated, and then centrifuged at 12,000×g. The supernatants were acidified and neutralized to pH 7.4 before assaying. The tissue levels of GDNF were measured with an ELISA kit (GDNF Emax ImmunoAssay System; Promega, Madison, Wis.), according to the protocol of the supplier. The levels of GDNF were expressed as picograms per milligram of protein. The assay sensitivity ranged from 16 to 1000 pg/ml.

Immunohistochemistry. Muscle sections (10 μm) were fixed in cold acetone, followed by incubation with rabbit anti-FLAG polyclonal antibodies (1:1000; Sigma, St. Louis, Mo.) as primary antibodies and biotinylated anti-rabbit antibodies as secondary ones (1:400; Santa Cruz Bio-technology, Santa Cruz, Calif.). Sections were visualized by the avidin-biotin peroxidase complex procedure (Vectastain ABC kits; Vector Laboratories, Burlingame, Calif.) using 3,3-diaminobenzidine as a chromogen.

For double-immunofluorescence staining of muscles, sections were sequentially incubated with blocking solution, polyclonal rabbit anti-FLAG antibodies (1:500; Sigma), FITC-conjugated goat anti-rabbit IgG (1:200; Santa Cruz Biotechnology), and tetramethylrhodamine-conjugated α-bungarotoxin (Molecular Probes, Eugene, Oreg.). Sections were examined and photographed under a confocal laser scanning microscope (TCS NT; Leica, Heidelberg, Germany).

For morphological analysis of the spinal cord, serial transverse sections (30 μm) were obtained for Nissl, SMI-32, or CTB immunostaining. Free-floating sections were immunohistochemically stained for SMI-32 with a Mouse-on-Mouse kit (M.O.M kit) (Vector Laboratories, Burlingame, Calif.), according to the protocol of the manufacturer. Sections processed for CTB immunoreactivity were blocked with 5% rabbit serum, followed by incubation with anti-CTB antibodies (1:10000, goat antiserum to CTB; List Biologic). Sections were visualized by standard ABC methods.

For double immunostaining of the spinal cord, sections were blocked with 10% normal goat serum and the blocking solution supplied with the M.O.M kit for 1 hr, respectively, and then sequentially incubated with polyclonal rabbit anti-FLAG antibodies (1:250; Sigma) and monoclonal mouse anti-SMI-32 antibodies (1:500) overnight at 4° C. After incubation with FITC-conjugated goat anti-rabbit IgG (mouse absorbed, 1:200; Santa Cruz Biotechnology) and rhodamine-conjugated goat anti-mouse IgG (1:200; Santa Cruz Biotechnology) for 2 hr at room temperature, the sections were examined and photographed under confocal laser scanning microscope.

Morphometric analysis and cell counting. Morphometric analysis was performed on images captured with a CCD camera using KS 400 image analysis software (Zeiss, Oberkochen, Germany). The mean area of muscle fibers was calculated from counts of >1000 fibers in randomly selected areas. To compare the number of motoneurons in the spinal cord, neurons were counted in Nissl-stained and SMI-32- and CTB-immunostained sections spanning the cervical and lumbrosacral enlargements in each group, as described previously (Lewis et al., Nat. Genet. (2000) 25:402–405). For each mouse, at least 20 sections in each sixth serial section were subjected to counting. Only large cell profiles meeting the following criteria were included: location in the ventral horn below a lateral line from the central canal, containing a distinct nucleus with a nucleolus, and possession of at least one thick process.

Statistical analyses. The data were statistically analyzed using repeated-measures ANOVA, followed by a Tukey's honestly significance difference test for multiple comparisons between groups (StatView 5.0 software; SAS, Cary, N.C.).

B. Results

GDNF Transgene Expression in Muscles of ALS Mice

The amount of GDNF in gastrocnemius muscles was determined by ELISA using the methods described above. At 110 days of age (7 weeks after injection), the GDNF levels in AAV-GDNF vector-treated mice were 7985.0±874.0 pg/mg protein, which is >120-fold higher than that in the control ALS group (62.2±20.5 pg/mg protein; $p<0.01$; n=4). At the time of death, AAV-GDNF vector-treated ALS mice tended to show a decrease in intramuscular GDNF expression (3281.7±667.0 pg/mg protein; n=4). The reduction of GDNF was assumed to be attributable to the severe atrophy of the transduced muscle fibers in ALS mice, because stable GDNF expression can last for at least 8 months in age-matched wild-type mice. These data suggested that AAV-GDNF vector could drive substantial transgenic GDNF expression in ALS mice until the end stage of the disease.

The pattern of distribution of transgenic GDNF in muscles was examined by means of immunodetection. FLAG was used as a tag to distinguish transgene GDNF from its endogenous counterpart. In AAV-GDNF vector-injected mice, strong FLAG immunoreactivity was detected in a large number of myofibers, both at 110 days of age and at the end stage of the disease. Punctured and reticular staining was observed in transverse sections of muscles, with intense immunoreactivity mainly localized in the vicinity of the sarcolemma, indicating that transgene-derived GDNF was efficiently secreted into the surrounding regions. Substantial FLAG signals could still be detected in atrophied myofibers at the end stage of the disease.

Furthermore, double-immunofluorescence staining with anti-FLAG antibodies and α-bungarotoxin was performed. α-Bungarotoxin is a molecular probe that specifically binds to the acetylcholine receptor (AChR) with high affinity on the postsynaptic membranes of NMJs. The results showed that more intense immunoreactivity for FLAG was colocalized with α-bungarotoxin signals, indicating that transgene GDNF was concentrated primarily in the regions of NMJs. As expected, the muscles treated with AAV-LacZ vector or the vehicle exhibited no immunostaining for anti-FLAG at any time point.

Preservation of Vector-treated Muscles

At 110 days of age, the gastrocnemius muscles in the control ALS mice weighed only approximately half those in the age-matched wild-type mice ($95.8\pm19.4$ vs $183.0\pm22.2$ mg; n=5). However, the gastrocnemius muscles of AAV-GDNF vector-treated ALS mice were approximately 1.68 times ($160.1\pm32.9$ mg; $p<0.01$; n=5) heavier than those of control ALS mice at the same age.

Figure 3:
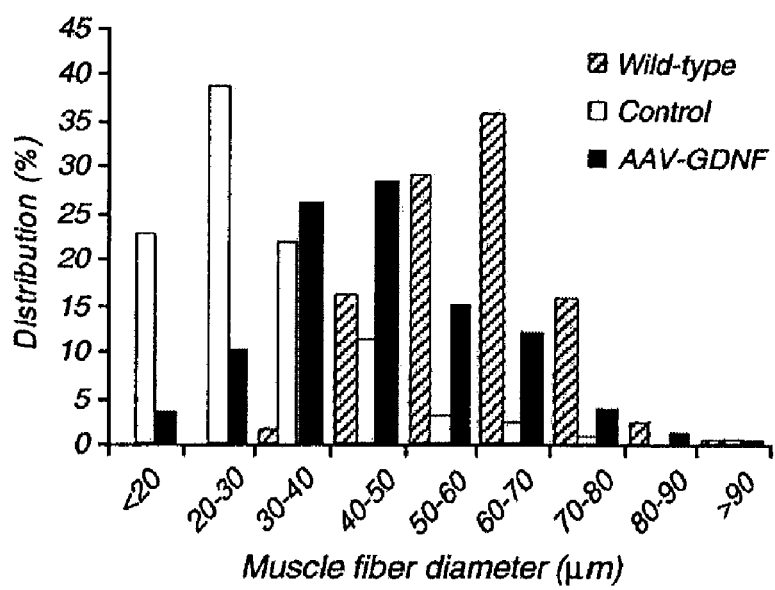
FIG. 3 displays percent distribution of muscle fibers of various diameters in wild-type, control ALS and AAV-GDNF-treated ALS mice.

Histological analysis of muscles in control ALS mice at 110 days of age revealed widespread groups of small, acutely angulated fibers, consistent with severe neurogenic atrophy. The mean myofiber area was greatly decreased ($1053.8\pm581.0$ $\mu m^2$; n=4), being approximately 30% of that in age-matched wild-type mice ($3517.6\pm613.5$ $\mu m^2$; n=5). In contrast, the muscles treated with AAV-GDNF vector showed little evidence of neurogenic atrophy with a more consistent fiber size, the mean myofiber area ($2252.8\pm1035.2$ $\mu m^2$; n=5) reaching approximately 71% of that in wild-type mice and more than two times that in the control ALS group. Additionally, the notable shift of myofibers toward a smaller diameter observed in control ALS mice was evidently moderated in the AAV-GDNF vector-treated group (FIG. 3), and the percentage of atrophied myofibers of <20 μm was significantly decreased (24% in control ALS group vs 9% in AAV-GDNF-treated group).

Retrograde Transport of Transgenic GDNF into Spinal Motoneurons

Retrograde axonal transport of GDNF into spinal lumbar motoneurons has been demonstrated in adult rats (Leitner et al., *J. Neurosci.* (1999) 19:9322–9331). Thus, the ability of transgene GDNF to be retrogradely transported to spinal motoneurons in ALS mice was examined. For this purpose, the FLAG tag in transgene GDNF was used to avoid interference of the results by endogenous GDNF. SMI-32 is a well characterized antibody that specifically recognizes nonphosphorylated neurofilaments (NP-NFs) and therefore serves as a reliable marker for motoneurons (Carriedo et al., *J. Neurosci.* (1996) 16:4069–4079). Thus, double immunostaining was performed with SMI-32 and FLAG antibodies on spinal cord sections from ALS mice. At 110 days of age, FLAG immunosignals could be detected in SMI-32-positive cells in the corresponding ventral horn in ALS mice at 7 weeks after intramuscular AAV-GDNF vector injection, whereas no FLAG signal was detected in the spinal cords of the control group ALS mice. This was further demonstrated in the subgroup of unilaterally treated ALS mice; FLAG signals could only be detected in motoneurons of the ventral horn ipsilateral to the AAV-GDNF vector-injected side and none in those on the contralateral AAV-LacZ vector-injected side. Although β-galactosidase signals were widely detected in AAV-LacZ vector-injected muscles, they were not observed at all in the corresponding ventral horn of the spinal cord.

As explained above in Example 3, the transgene GDNF that appeared in the motoneurons could have been derived through three possible ways: systemic delivery, retrograde transport of AAV vectors, or retrograde transport of GDNF fusion protein itself. However, the restricted distribution and ipsilateral presentation of transgenic GDNF in motoneurons, as well as its known inability to pass through the blood-brain barrier, exclude the possibility of its systematic delivery to the spinal cord. To date, most reports show that AAV vectors are not retrogradely transported or are transported in only a very limited manner (Chamberlin et al., *Brain Res.* (1998) 793:169–175; Klein et al., *Exp. Neurol.* (1998) 150:183–194; Alisky et al., *NeuroReport* (2000) 11:2669–2673. One recent report, however, has revealed retrograde transport of an AAV vector itself in the CNS, a reporter green fluorescent protein being used as a tracer (Kaspar et al., *Mol. Ther.* (2002) 5:50–56). Thus, the possibility that AAV particles may also have been transported to the corresponding motoneurons cannot be completely ruled out. However, the vectors carried to the motoneurons, are assumed to be very limited because no β-galactosidase was detected in the corresponding spinal motoneurons, despite its wide distribution in the transduced muscles.

In contrast, the transgenic GDNF was abundantly detected in both transduced muscles and the corresponding motoneurons after AAV-GDNF injection. This finding, combined with the previous reports as well as the observation regarding β-galactosidase activity, indicates that the transgenic GDNF in the motoneurons is mainly derived through retrograde axonal transport of the GDNF protein. This is consistent with previous studies (Kordower et al., *Science* (2000) 290:767–773; Wang et al., *Gene Ther.* (2002) 9:381–389), showing that transgenic GDNF is retrogradely transported. The finding that transgenic GDNF in muscle fibers was predominantly accumulated to the regions of NMJs is also compatible with its retrograde transport hypothesized because it is in the axon terminals in which substances secreted from muscle fibers are taken up to be retrogradely transported.

Effect of Transgene GDNF on Spinal Motoneuron Survival

To assess the neuroprotective effect of GDNF on the survival of motoneurons, the numbers of spinal motoneurons in the different groups at 110 days of age were compared. Nissl staining of the spinal cord showed a severe loss of motoneurons in the ventral horns of the control ALS mice (FIG. 4A). In contrast, in AAV-GDNF vector-treated mice, a significantly larger number of motoneurons remained in both cervical and lumbar segments (FIG. 4A), suggesting a markedly protective effect of the transgenic GDNF on motoneurons.

Staining for NP-NF is a reliable means of assessing the extent of motoneuron loss in ALS, in which it has been shown that motoneuron degeneration induces dephosphorylation of NP-NF, resulting in SMI-32 staining resistance (Tsang et al., Brain Res. (2000) 861:45–58). Staining was performed on serial sections to evaluate motoneurons with NP-NF. Consistent with the Nissl-staining results, AAV-GDNF vector-treated ALS mice had significantly greater numbers of SMI-32-positive motoneurons compared with in the control ALS group (FIG. 4B). Thus, the motoneuron degeneration, as well as the aberrant NF dephosphorylation in the spinal cord ventral horn of ALS mice, was also significantly inhibited after AAV-GDNF vector administration. Thus, both SMI-32 staining and Nissl staining confirmed significant rescue of motoneurons by AAV-GDNF vector delivery.

In the unilaterally treated subgroup of ALS mice killed at 110 days of age, many more motoneurons survived in the lumbar spinal cord ventral horns ipsilateral to the AAV-GDNF vector-injected side than on the contralateral side treated with AAV-LacZ vector (Nissl staining, 17.1±3.2 vs 10.3±1.1; SMI-32-positive neurons, 15.6±1.8 vs 8.8±3.2; p<0.01; n=5). Thus, these findings further suggested that the therapeutic effect on motoneurons resulted from retrograde transport of transgenic GDNF on the same side rather than from systemic delivery.

Effect on the Maintenance of Motoneuron Axonal Projections to Muscles

To further quantitatively assess surviving motoneurons that retained functioning neuromuscular projections to the injected muscles, such motoneurons were selectively labeled by injection of a neural tracer CTB into the bilateral gastrocnemius muscles of mice 1 week before being sacrificed. At 110 days of age, there were much fewer CTB-labeled motoneurons in control ALS mice than in wild-type mice. However, with AAV-GDNF vector treatment, more CTB-labeled motoneurons were maintained than in the control ALS group (20.7±4.9 vs 11.0±2.5%; n=4; p<0.01) (FIG. 5A). Transgenic GDNF delivery to muscle thus played an important role in the maintenance of the axonal projections of corresponding motoneurons.

For more accurate morphometric evaluation of surviving motoneurons labeled with CTB, we next determined the size and distribution of such neurons in the lumbar spinal cord. The control group of ALS mice killed at 110 d of age exhibited a significantly smaller mean area of CTB-labeled neurons than that in age-matched wild-type mice (353.1±173.8 vs 733.7±252.0 $\mu m^2$; n=4; p<0.01), the size distribution being shifted toward smaller ones, indicating significant atrophy of CTB-positive motoneurons (FIG. 5B). In contrast, AAV-GDNF vector treatment of ALS mice markedly decreased the motoneuron atrophy (605.8±248.2 $\mu m^2$; n=4; p<0.01 vs control group), and the size distribution shifted toward smaller ones. Together, these results show that GDNF gene delivery to muscles can promote the survival and inhibit the atrophy of motoneurons with axonal projections to target muscles in ALS mice.

Because CTB can be axonally transported to neuronal cell bodies in a retrograde direction and be detected throughout the neuronal cytoplasm (Llewellyn-Smith et al., J. Neurosci. Meth. (2000) 103:83–90), the detection of CTB-positive motoneurons means that they maintain intact axonal connection with the AAV-GDNF vector-injected muscles. Thus, CTB labeling makes it possible to assess the effect of the transgenic GDNF on the spinal motoneurons more accurately than with Nissl or NP-NF staining alone. This method revealed greater numbers of larger spinal motoneurons labeled with CTB in AAV-GDNF vector-treated ALS mice. These findings together indicate that intramuscular injection of AAV-GDNF vector can delay the degeneration of motoneurons, thereby allowing prolonged functioning axons in ALS mice.

Figure 6A:
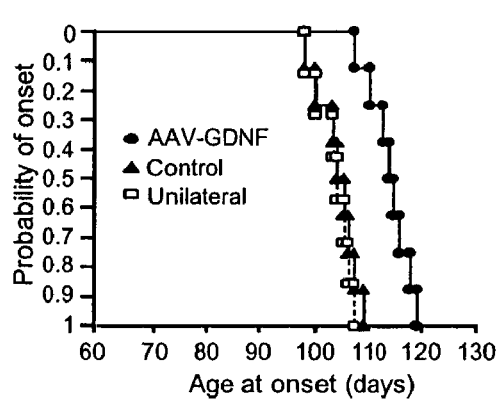
FIGS. 6A–6E show the results of experiments demonstrating that GDNF delays the onset of disease, improves motor performance, and prolongs survival in transgenic ALS mice.
Figure 6B:
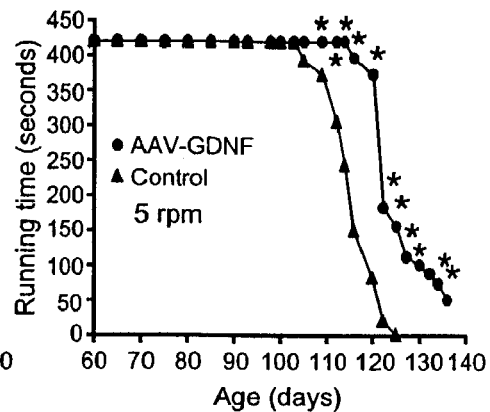
Figure 6C:
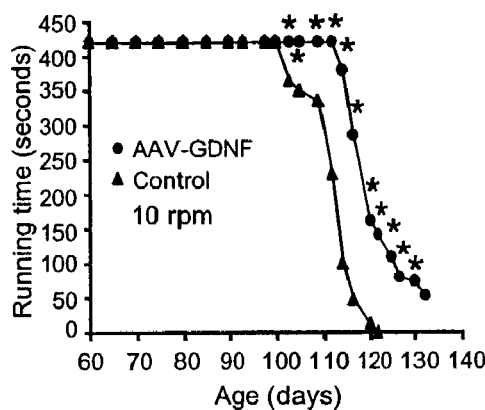
Figure 6D:
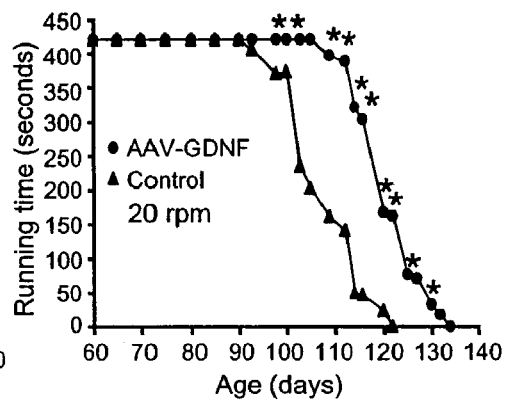
Figure 6E:
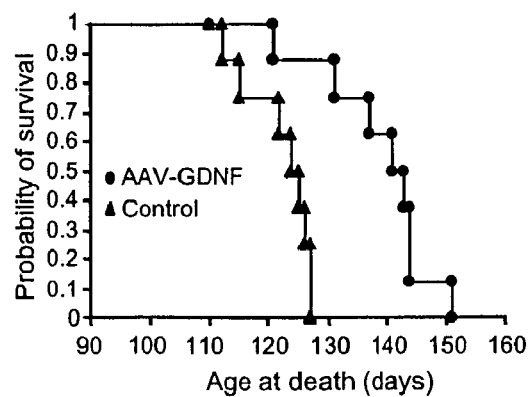

GDNF Delays the Onset of Disease, Improves Motor Performance, and Prolongs Survival in Transgenic ALS Mice Any group of ALS mice that had AAV-GDNF vector, AAV-LacZ vector, or the vehicle injected in the four limbs at 9 weeks of age showed similar motor performance, as quantified with a rotarod, until 12 weeks of age. Thereafter, it deteriorated quickly in control ALS mice, whereas the performance deterioration was significantly delayed in AAV-GDNF vector-treated mice (p<0.05) (FIGS. 6A–6D), indicating significantly prolonged maintenance of their motor strength. The average age of motor deficit onset in AAV-GDNF vector-treated ALS mice was 114.0±4.0 d (n=12), whereas it was 101.3±5.4 d (n=11) in control ALS mice, the difference being significant (p<0.01) (FIG. 6A). AAV-GDNF vector treatment prolonged the mean survival by 16.6±4.1 d compared with in the control ALS mice (138.9±9.2 d in AAV-GDNF vector-treated mice vs 122.3±5.7 d in control ALS mice; n=8; p<0.01) (FIG. 6E). These results mean that bilateral intramuscular injection of AAV-GDNF vector delayed the onset of disease by approximately 13% and prolonged the survival of transgenic ALS mice by approximately 14%.

However, weakness and atrophy of the skeletal muscles, especially in the hindlimbs, ultimately developed in all mice of all groups once motor symptoms had appeared. The duration of the disease, as evaluated as the number of days that elapsed from the onset to the end stage, did not differ between the AAV-GDNF vector-treated and control ALS mice (24.0±3.5 vs 21.0±3.5 d; p>0.05). Because GDNF is a secreted protein, we assessed whether the therapeutic benefit of transgene-derived GDNF also resulted from systemic circulation after AAV-GDNF vector administration or not. In a subgroup of unilaterally treated ALS mice that had AAV-GDNF vector injected into their left limbs and AAV-LacZ vector injected into their right ones, each mouse moved the AAV-GDNF vector-injected limbs almost normally until 110 days of age. However, the contralateral limbs developed muscle weakness at as early as 93 days of age, there being a waddling gait. Despite the better motor functions of AAV-GDNF vector-treated limbs, the mice showed no significant difference in the running time on a rotarod at any speed tested compared with the control ALS mice. The average onset time of motor deficit in this subgroup also showed no significant difference compared with in the control ALS group (102.7±3.1 d; n=7; p>0.05) (FIG. 6D).

To summarize, AAV-GDNF vector-treated ALS mice with four-limb injections, in contrast to the control ALS group, showed much better behavioral performance, with delayed onset of disease and a prolonged life span, which is in agreement with the attenuation of the motoneuron pathology. In the subgroup with unilateral AAV-GDNF treatment, the therapeutic effects of GDNF on behavioral and pathological features were limited to the same treated side, with obvious deterioration of motor performance on the AAV-LacZ vector-treated side. However, the motor performance on a rotarod and the onset of disease remained similar to those in the control group. Thus, it is assumed that the therapeutic benefit mostly resulted from direct action of transgenic GDNF on motoneurons after its retrograde transport rather than from the systemic delivery.

Although bilateral administration of AAV-GDNF vector markedly delayed the onset of disease and improved the survival of ALS mice, it failed to prolong the length of time from disease onset to death. What is more, despite the substantial expression of GDNF, the AAV-GDNF vector-treated mice ultimately reached the end stage, when morphological assessment demonstrated such severe atrophy of myofibers and massive loss of spinal motoneurons as in the control ALS mice. It has been reported that pathological changes occur at asymptomatic stages in ALS mice, and massive motoneuron death occurs at the end stage (Dal Canto and Gurney, *Brain Res.* (1995) 676:25–40; Wong et al., *Neuron* (1995) 14:1105–1116; Mourelatos et al., *Proc. Natl. Acad. Sci. USA* (1996) 93:5472–5477; Tu et al., *Proc. Natl. Acad. Sci. USA* (1996) 93:3155–3160; Bruijn et al., *Science* (1998) 281:1851–1854; Shibata et al., *Acta. Neuropathol.* (1998) 95:136–142). Thus, the transgene GDNF may exhibit its greatest protective function for motoneurons in ALS mice at asymptomatic stages when the ventral horns have a mild pathology. Once the disease develops, however, GDNF gene therapy may not as readily inhibit the massive motoneuron death or interfere with the rapidly inevitable progression of the disease. In the above experiment, treatment was begun at the age of 9 weeks. Administration of GDNF at earlier times and/or together with other neurotrophic factors (Bilak et al., *Amyotroph. Lateral Scler. Other Motor Neuron Disord.* (2001) 2:83–91) may lead to better results.

The above studies show that intramuscular injection of AAV-GDNF vector into the transgenic ALS mice model results in sustained substantial biosynthesis of GDNF in the muscles and retrograde transport to the corresponding spinal motoneurons. Expression was sustained until the terminal stage in ALS mice, likely guaranteeing a continual supply of biologically synthesized GDNF to the motoneuronal axon terminals in the muscles. Furthermore, this transgene expression not only significantly prevented the loss of motoneurons but also lead to marked attenuation of the manifestation of the disease and prolonged survival of the transgenic ALS mice. Additionally, AAV-GDNF vector-treated ALS mice, in contrast to the control ALS group, showed much better behavioral performance.

Accordingly, novel methods for treating motoneuron diseases, such as ALS, are provided. Although preferred embodiments of the subject invention have been described in some detail, it is understood that obvious variations can be made without departing from the spirit and the scope of the invention as defined by the appended claims.

We claim:

1. A method of delivering a recombinant adeno-associated virus (AAV) virion to a muscle cell or muscle tissue of a mammalian subject with amyotrophic lateral sclerosis, said method comprising:
    (a) providing a recombinant AAV virion which comprises a polynucleotide encoding a glial cell line-derived neurotrophic factor (GDNF) operably linked to control elements capable of directing the in vivo transcription and translation of said GDNF; and
    (b) delivering said recombinant AAV virion directly into said muscle cell or muscle tissue of said subject, whereby said GDNF is expressed at a level which provides a therapeutic effect in said mammalian subject.

2. The method of claim 1, wherein said recombinant AAV virion is introduced by intramuscular injection.

3. A method of delivering a recombinant adeno-associated virus (AAV) virion to a skeletal muscle of a human subject with amyotrophic lateral sclerosis, said method comprising:
    (a) providing a recombinant AAV virion, said recombinant AAV virion comprising a polynucleotide encoding a human glial cell line-derived neurotrophic factor (GDNF) operably linked to control elements capable of directing the in vivo transcription and translation of said GDNF; and
    (b) delivering said recombinant AAV virion directly into skeletal muscle of said subject in vivo, whereby said GDNF is expressed at a level which provides a therapeutic effect in said human subject.

4. A method of treating a mammalian subject with amyotrophic lateral sclerosis, said method comprising administering into skeletal muscle of said subject a composition comprising recombinant adeno-associated virus (AAV) virions that comprise a polynucleotide encoding a glial cell line-derived neurotrophic factor (GDNF) polypeptide operably linked to expression control elements capable of directing the in vivo transcription and translation of said GDNF, to provide a therapeutic effect.

5. The method of claim 4, wherein the polynucleotide encodes human pre-pro-GDNF.

6. The method of claim 4, wherein the control elements comprise a viral promoter.

7. The method of claim 6, wherein the promoter is an MLP, CMV, or RSV LTR promoter.

* * * * *